United States Patent

Sekino et al.

[11] Patent Number: 5,328,458
[45] Date of Patent: Jul. 12, 1994

[54] INSUFFLATION APPARATUS

[75] Inventors: Naomi Sekino, Tokyo; Kenji Noda, Sagamihara; Yutaka Yanagawa, Tokyo; Takeo Usui, Tokyo; Kouji Tanikawa, Tokyo; Kazuhiro Takahashi, Tokyo; Shiro Bito, Tokyo, all of Japan

[73] Assignee: Olympus Optical Co., Ltd., Tokyo, Japan

[21] Appl. No.: 984,306

[22] Filed: Nov. 30, 1992

[30] Foreign Application Priority Data

Dec. 3, 1991 [JP] Japan .................. 3-318910
Dec. 5, 1991 [JP] Japan .................. 3-322002
May 29, 1992 [JP] Japan .................. 4-139434
May 29, 1992 [JP] Japan .................. 4-139451

[51] Int. Cl.⁵ .......................... A61M 37/00
[52] U.S. Cl. .......................... 604/23; 604/26; 604/66; 604/67; 604/65
[58] Field of Search .......... 128/747, 748; 604/23, 604/24, 25, 26, 66, 67, 65

[56] References Cited

U.S. PATENT DOCUMENTS

| | | | |
|---|---|---|---|
| 3,553,625 | 1/1971 | Stedman | 128/748 |
| 4,023,562 | 5/1977 | Hynecek et al. | 128/748 |
| 4,207,887 | 6/1980 | Hiltebrandt et al. | 604/26 |
| 4,464,169 | 8/1984 | Semm | 604/26 |
| 4,971,034 | 11/1990 | Doi et al. | 128/6 |
| 5,152,745 | 10/1992 | Steiner et al. | 604/26 |
| 5,209,721 | 5/1993 | Wilk | 604/26 |

FOREIGN PATENT DOCUMENTS

3000218C2 6/1983 Fed. Rep. of Germany .

Primary Examiner—C. Fred Rosenbaum
Assistant Examiner—N. Kent Gring
Attorney, Agent, or Firm—Frishauf, Holtz, Goodman & Woodward

[57] ABSTRACT

An insufflation apparatus intended to insufflate gas supplied from a gas supply source into a cavity of the human body through a gas insufflating pipe, comprising a switch valve for opening and closing a gas supply pipe extending from the gas supply source to the gas insufflating pipe, a cavity pressure measuring unit arranged in the gas supply pipe to measure the pressure in the body cavity, a pressure setting section for setting an intended pressure in the body cavity, an arithmetic unit for calculating the difference of a value measured by the cavity pressure measuring unit relative to the value of pressure set by the pressure setting section, and a changeover control unit for changing over the timings at which the switch valve is opened and closed on the basis of values thus calculated by the arithmetic unit.

18 Claims, 14 Drawing Sheets

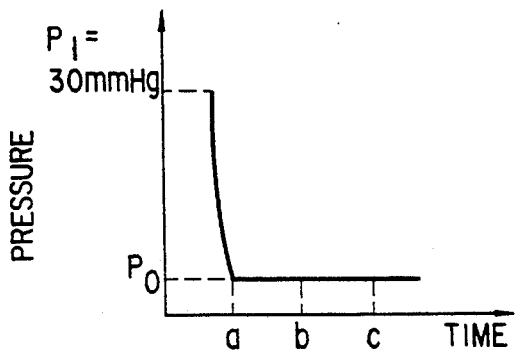
F I G. 9
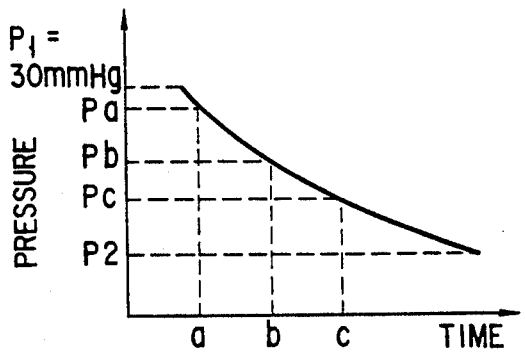
F I G. 10
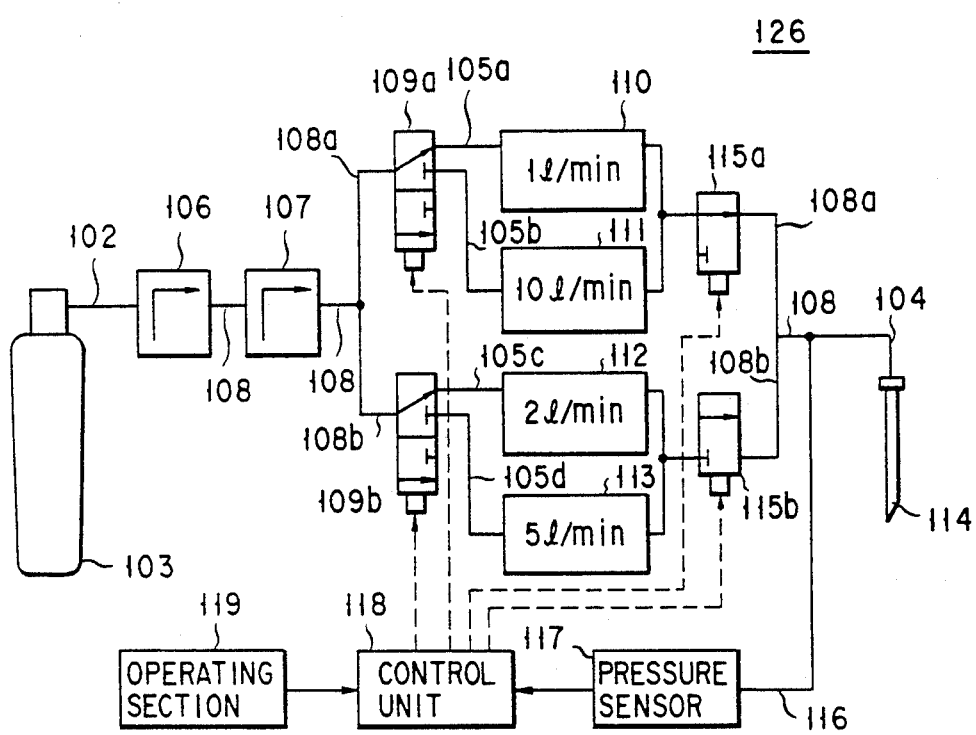
F I G. 11

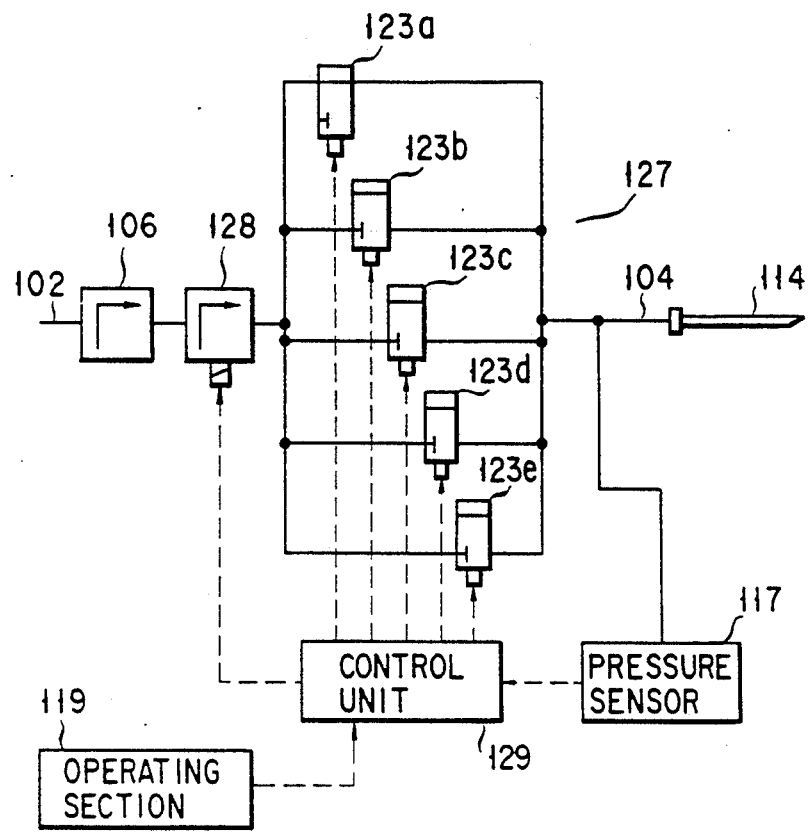
F I G. 12
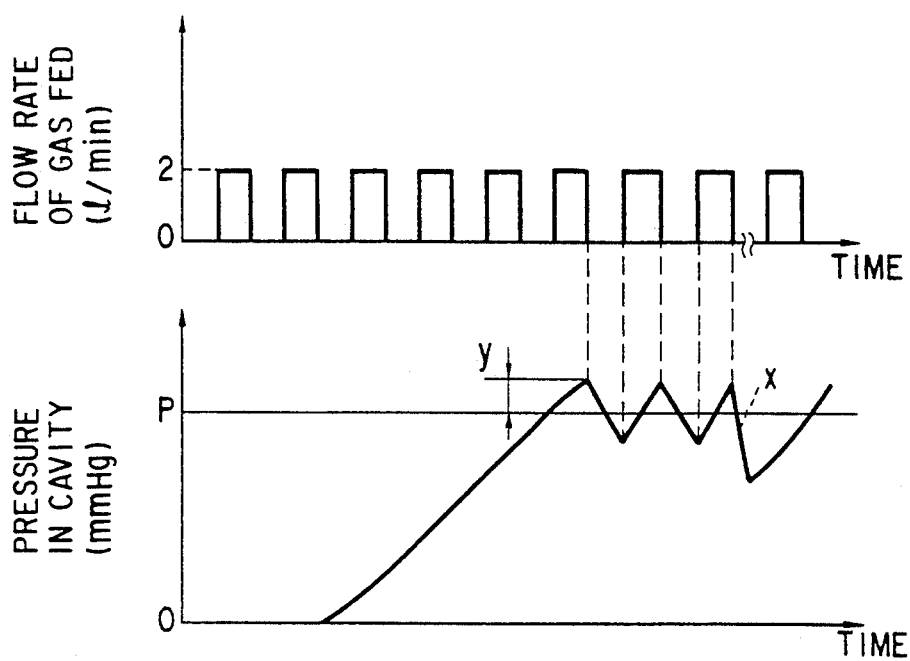
F I G. 13

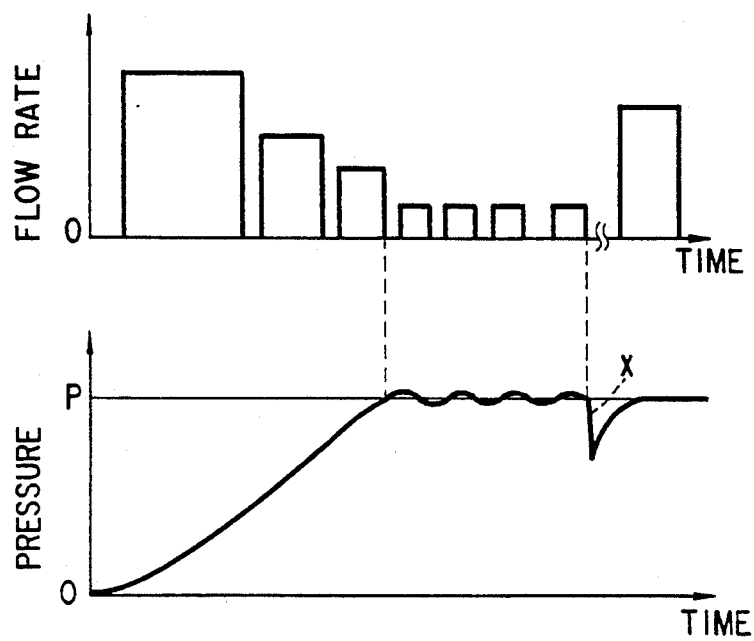
F I G. 14
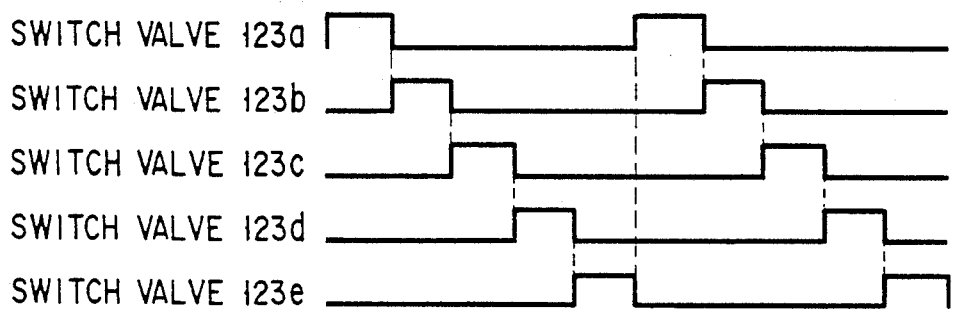
F I G. 15
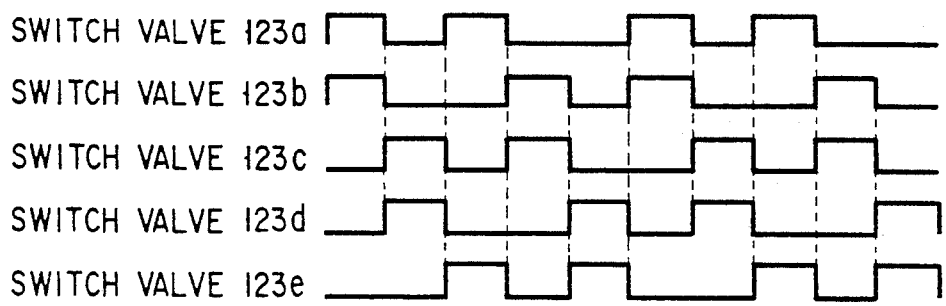
F I G. 16

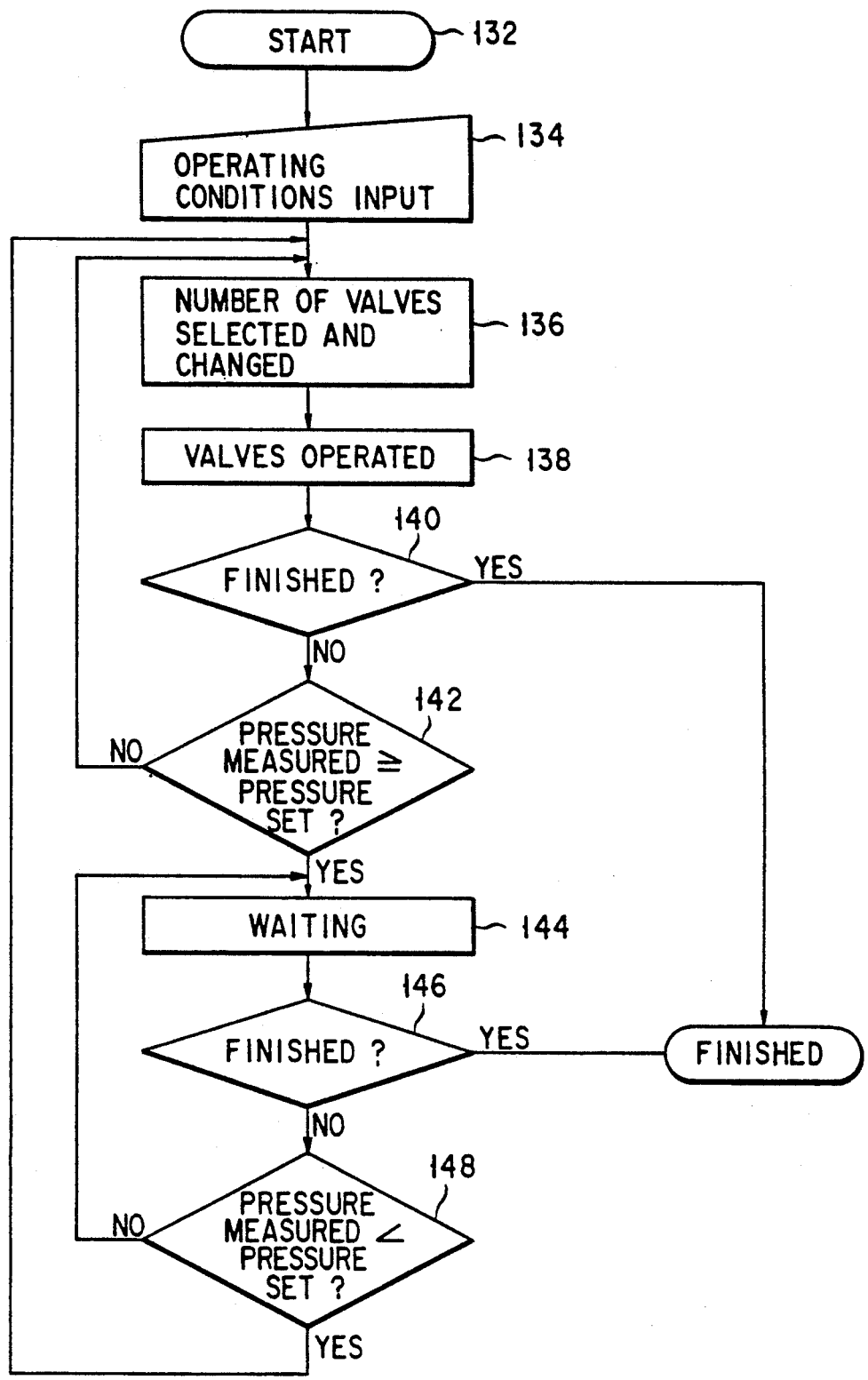
F I G. 17

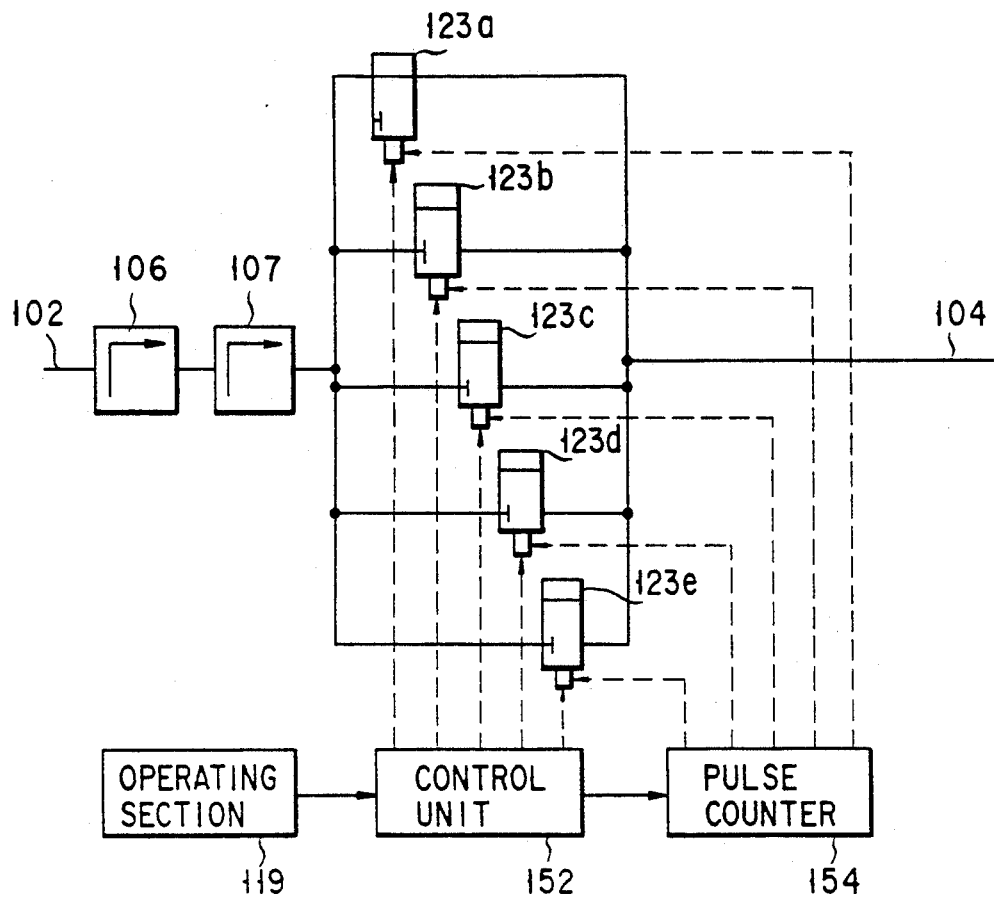
F I G. 18
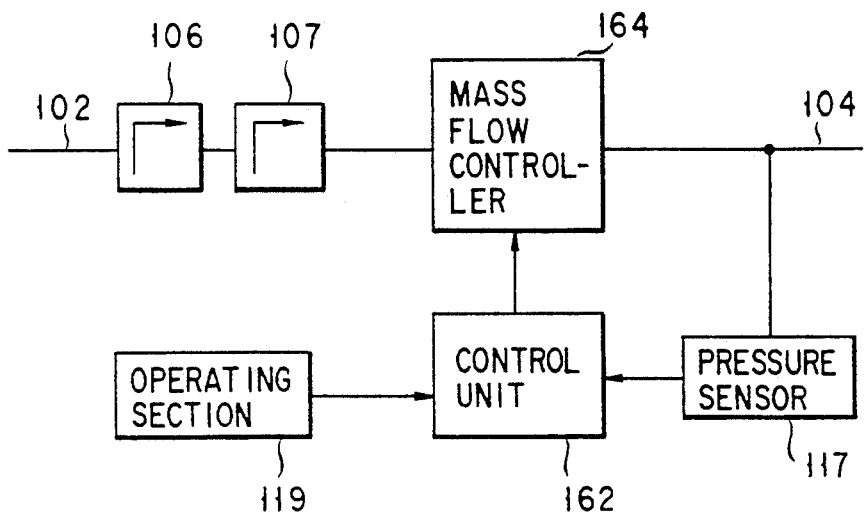
F I G. 19

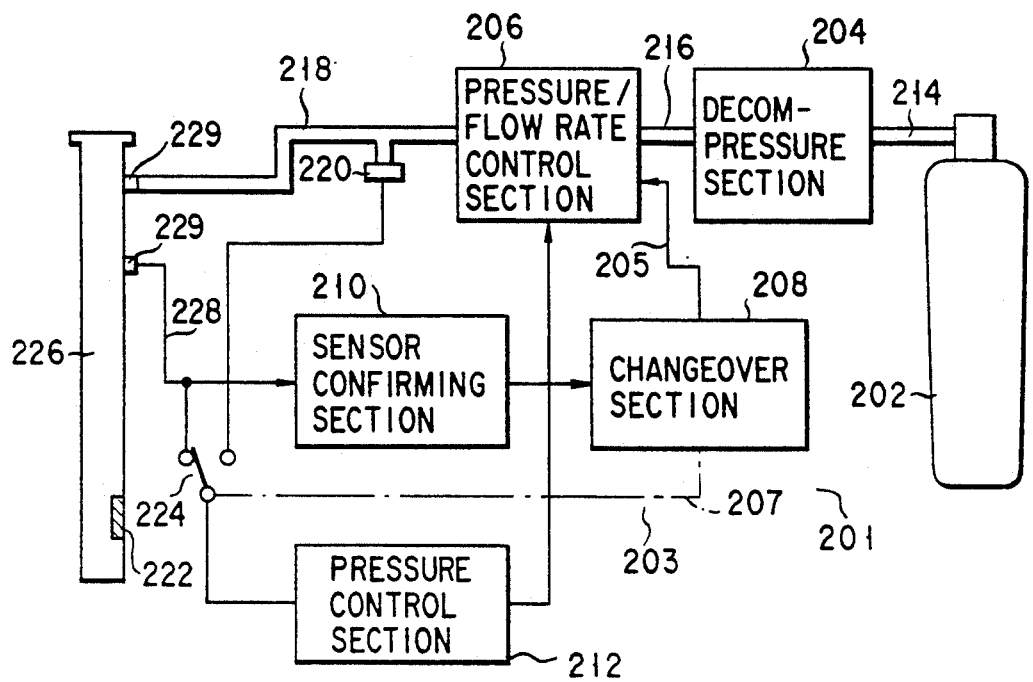
F I G. 20
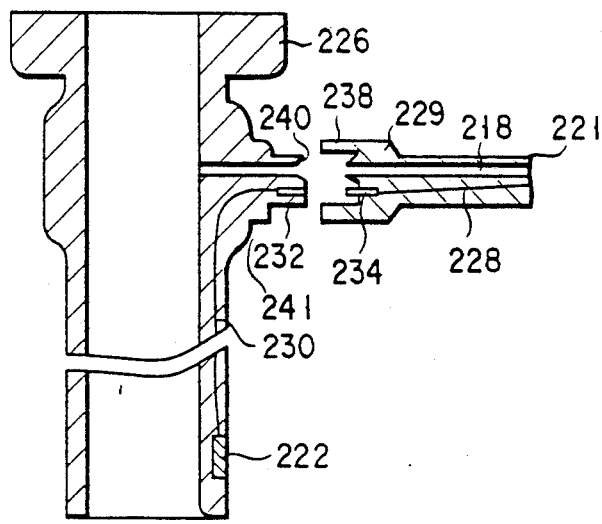
F I G. 21
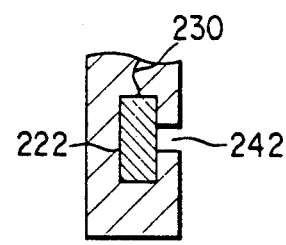
F I G. 22

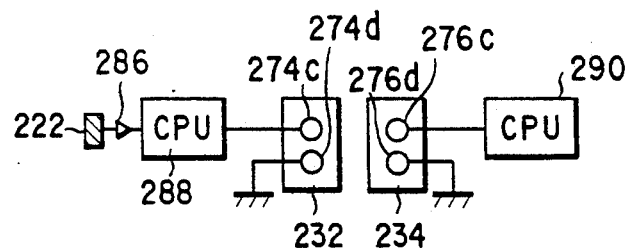
F I G. 27
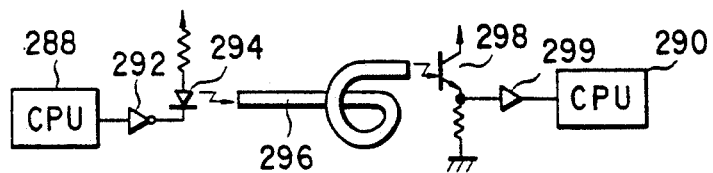
F I G. 28
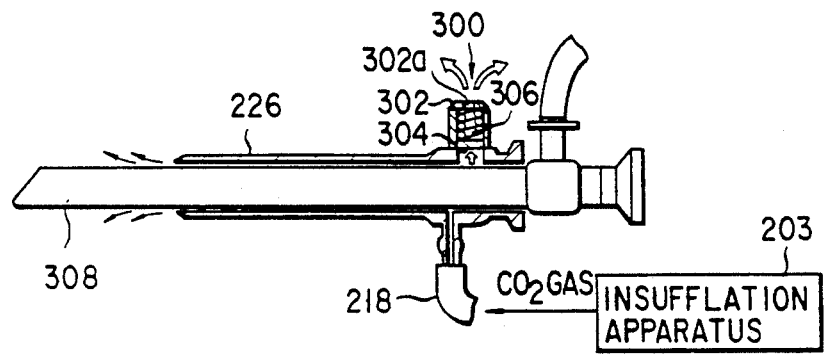
F I G. 29
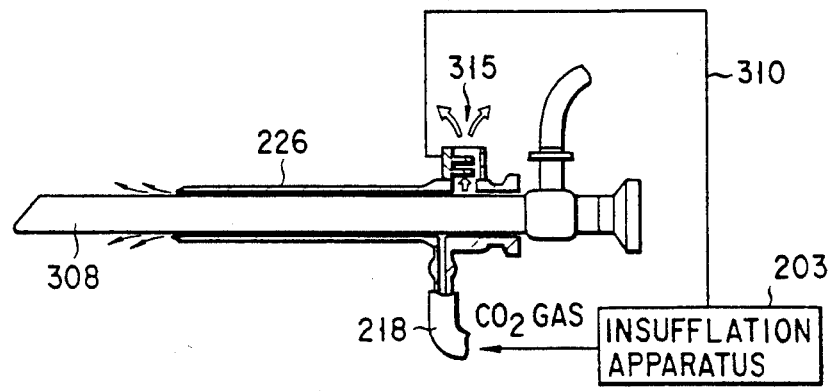
F I G. 30

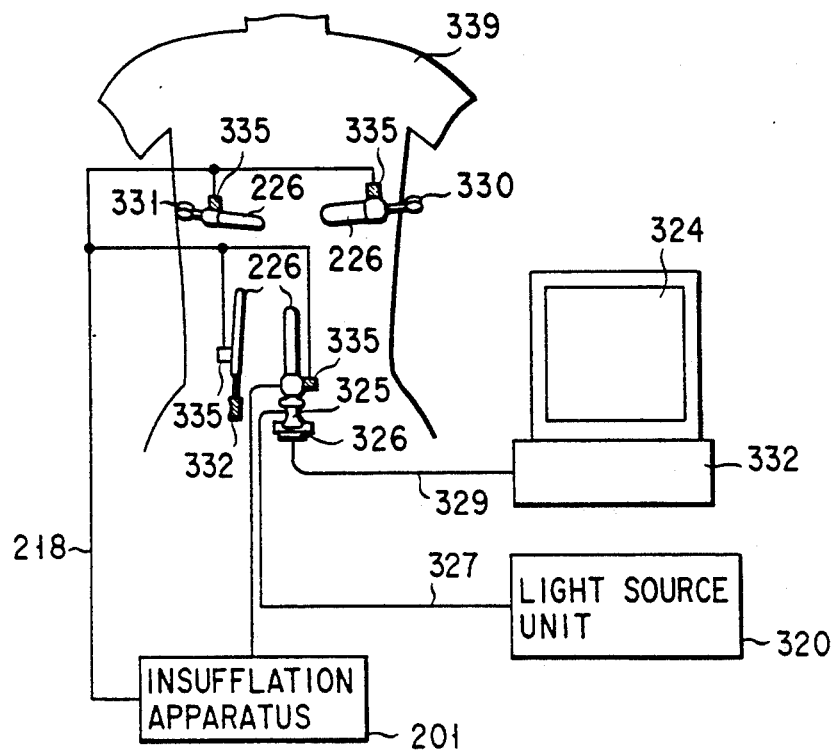
F I G. 31
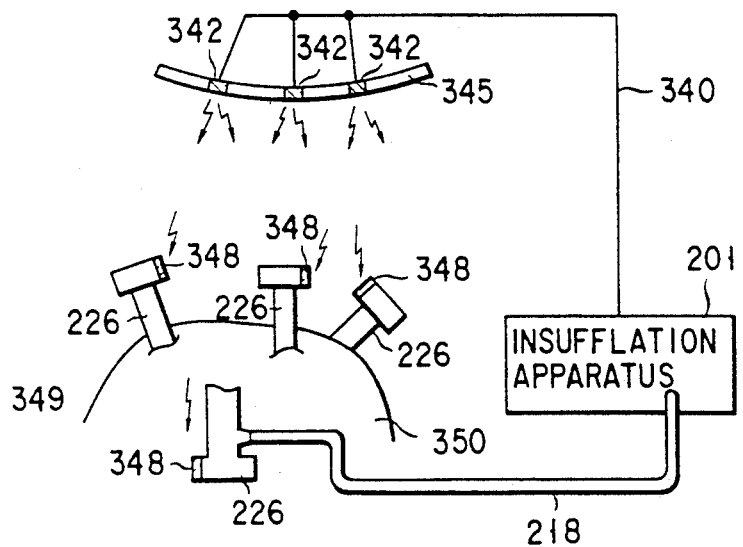
F I G. 32

INSUFFLATION APPARATUS

BACKGROUND OF THE INVENTION

1. Field of the Invention

The present invention relates to an insufflation apparatus intended to enlarge an intended part in a cavity of the human body, while insufflating gas into the body cavity, to obtain a field of vision, through the endoscope, necessary to add a therapeutical and surgical treatment to that part in the body cavity.

2. Description of the Related Art

When the therapeutical and surgical treatment is to be added to the intended part in the body cavity, while viewing that part through the endoscope, for example, gas such as $CO_2$ gas is insufflated into the body cavity to enlarge that part in the body cavity which is to be treated. A field of vision necessary to add the surgical treatment to the intended part in the body cavity is thus obtained so that it can be grasped enough how the surgical treatment advances in the body cavity.

In order to insufflate gas into the body cavity, the insufflation apparatus is used. It serves in this case to keep the pressure in the body cavity at a value set while controlling the pressure of gas supplied from a gas supply source such as the gas bomb by means of valves and decompression means.

Some of these insufflation apparatuses are disclosed in German Patent Publication No. 3000218 and German Patent Pre-opened Disclosure No. 3611018.

In the case of the former, one or more of plural gas insufflating pipes having the same flow rate is or are selected to adjust the flow rate of gas insufflated, and the amount of gas insufflated and the pressure in the body cavity are alternately measured. In the case of the latter, a decompression means is provided to adjust the operating pressure in a single gas insufflating pipe through an electric control circuit and the decompressing operation of this decompression means is changed to control the amount of gas insufflated into the body cavity without using any electromagnetic valve.

In the case of these insufflation apparatuses disclosed in the German Patent Publication and Application, however, the pressure of gas insufflated is low or about 50 mmHg. Therefore, the maximum flow rate obtained is only about 6 lits/min and this makes it difficult to insufflate gas into the body cavity at high speed.

Further, when the pressure of gas insufflated is made higher than 100 mmHg, for example, in the abovementioned insufflation apparatuses, the pressure in the body cavity is likely to exceed the value of pressure set, particularly in a case where the value of pressure set is small.

SUMMARY OF THE INVENTION

The object of the present invention is therefore to provide an insufflation apparatus capable of insufflating gas into the body cavity at high speed whatever value the pressure of gas insufflated may be set, and also capable of controlling the pressure of gas insufflated so exactly as not to cause the pressure in the body cavity to exceed the value of pressure set.

This object of the present invention can be achieved by an insufflation apparatus comprising a gas supply pipe through which gas supplied from a gas supply source is insufflated into a gas insufflating pipe, a switch valve for opening and closing the gas supply pipe, a cavity pressure measuring unit arranged in the gas supply pipe to measure the pressure in the body cavity, a pressure setting section for setting an intended pressure in the body cavity, an arithmetic unit for calculating the difference of values measured by the cavity pressure measuring unit relative to the value of pressure set by the pressure setting section, and a control unit for changing the timings at which the switch valve is opened and closed on the basis of values thus calculated by the arithmetic unit.

According to the insufflation apparatus of the present invention, the flow rate of gas insufflated can be optionally changed, whatever value the pressure of gas insufflated may be set, when the control unit controls the switch valve to be opened and closed.

Further, when the insufflation apparatus includes pipe changeover means for optionally selecting one or more of plural flow rate adjusting pipes, which are arranged in the gas supply pipe and which have different flow rates per a time unit, to cause it or them to be opened, and changeover control means for controlling the pipe changeover means according to a flow rate of gas insufflated from the gas supply pipe into the gas insufflating pipe, the flow rate of gas insufflated can be changed in a wider range of values.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9 is a graph showing pressure drop in the intermediate tank at the initial gas insufflating stage;

FIG. 10 is a graph showing pressure drop in the intermediate tank at a stage at which the gas insufflation is advanced to some extent;

FIG. 11 is a circuit diagram showing the insufflation apparatus according to a third embodiment of the present invention;

FIG. 12 is a circuit diagram showing the insufflation apparatus according to a fourth embodiment of the present invention;

FIG. 13 is a graph showing how the flow rate of gas insufflated and the pressure in the body cavity change relative to time when the opening and closing of the electromagnetic valve are repeated at a certain time interval without controlling the flow rate of gas insufflated;

FIG. 14 is a graph showing how the flow rate of gas insufflated and the pressure in the body cavity change relative to time when the opening and closing of the electromagnetic valve are repeated at a certain time interval while controlling the flow rate of gas insufflated;

FIG. 15 is a time chart showing the changeover operations of plural electromagnetic valves;

FIG. 16 is a time chart showing other changeover operations of plural electromagnetic valves;

FIG. 17 is a flow chart showing how the electromagnetic valves are changed over in the insufflation apparatus shown in FIG. 12;

FIG. 18 is a circuit diagram showing a variation of the insufflation apparatus shown in FIG. 12;

FIG. 19 is a circuit diagram showing the insufflation apparatus according to a fifth embodiment of the present invention;

FIG. 20 is a circuit diagram showing an insufflation apparatus capable of changing over two cavity pressure measuring sections from each other;

FIG. 21 is a sectional view showing in detail how gas insufflating pipe (or trocar) is connected to an insufflation unit;

FIG. 22 is an enlarged sectional view showing a pressure sensor embedded in the gas insufflating pipe;

FIG. 27 is a circuit diagram showing a second variation of the components arrangement shown in FIG. 25;

FIG. 28 is a circuit diagram showing a third variation of the components arrangement shown in FIG. 25;

FIG. 29 is a sectional view showing a trocar provided with a relief valve of the spring type;

FIG. 30 is a sectional view showing a trocar provided with a relief valve of the electromagnetic type;

FIG. 31 schematically shows first danger preventing means employed by the insufflation apparatus;

FIG. 32 schematically shows second danger preventing means employed by the insufflation apparatus;

DETAILED DESCRIPTION OF THE PREFERRED EMBODIMENTS

Figure 1:
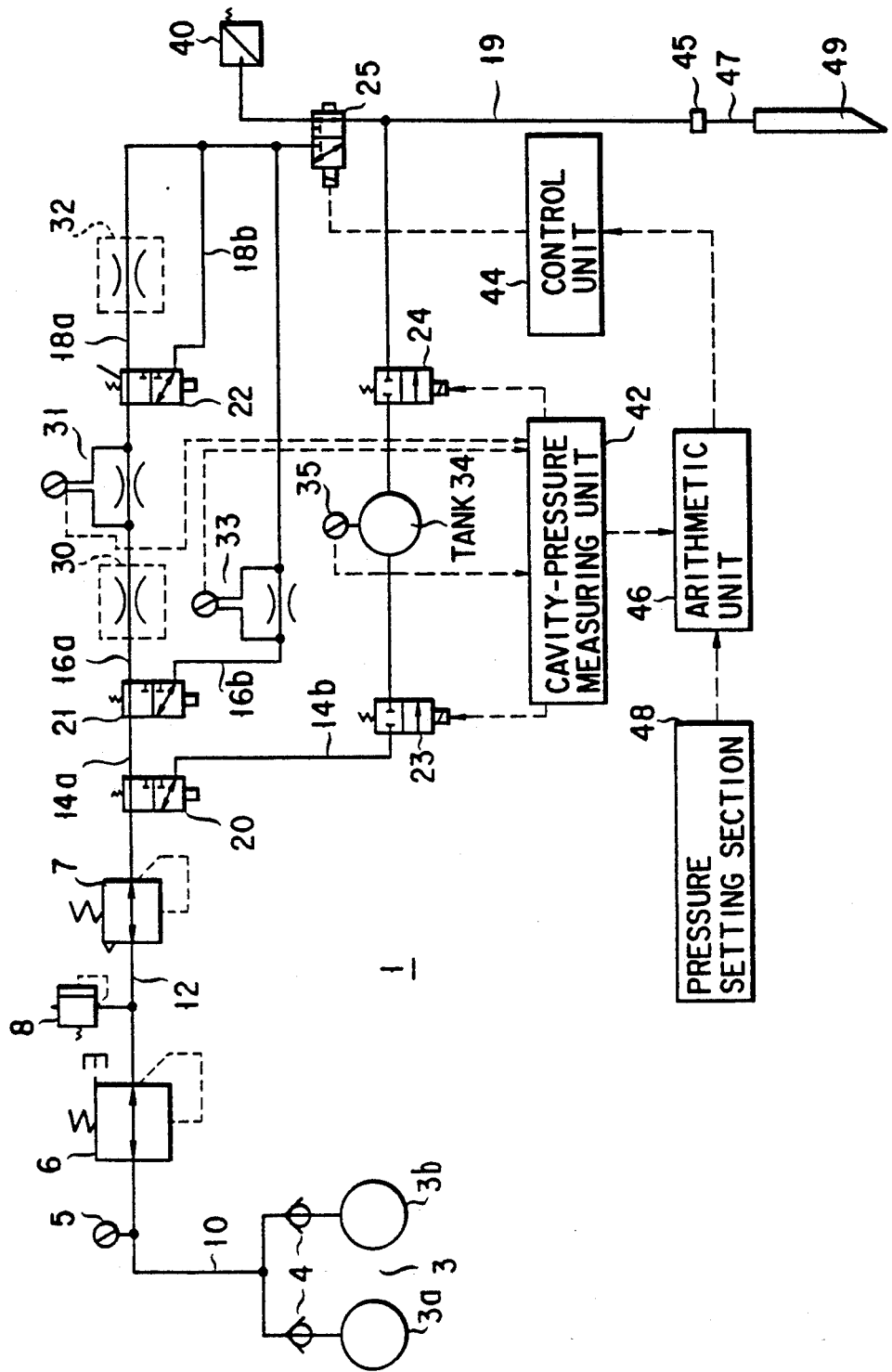
FIG. 1 is a circuit diagram showing the insufflation apparatus according to a first embodiment of the present invention.
Figure 2:
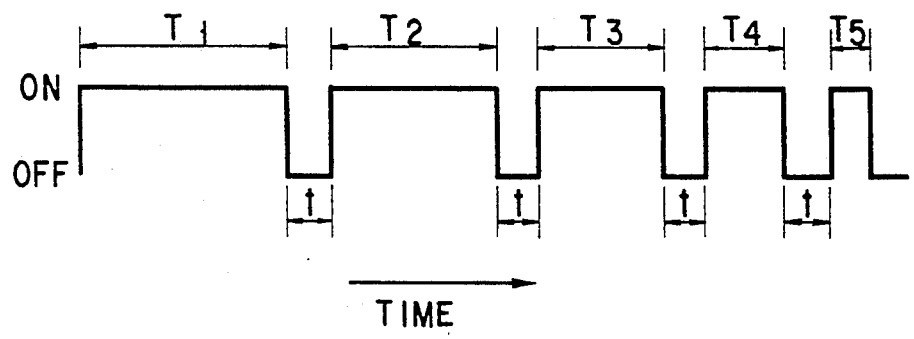
FIG. 2 is a time chart showing the timings at which a three-way electromagnetic valve is made ON and OFF and the pressure of gas insufflated is measured, said valve allowing $CO_2$ gas supplied from the insufflation apparatus to be insufflated through it.
Figure 3:
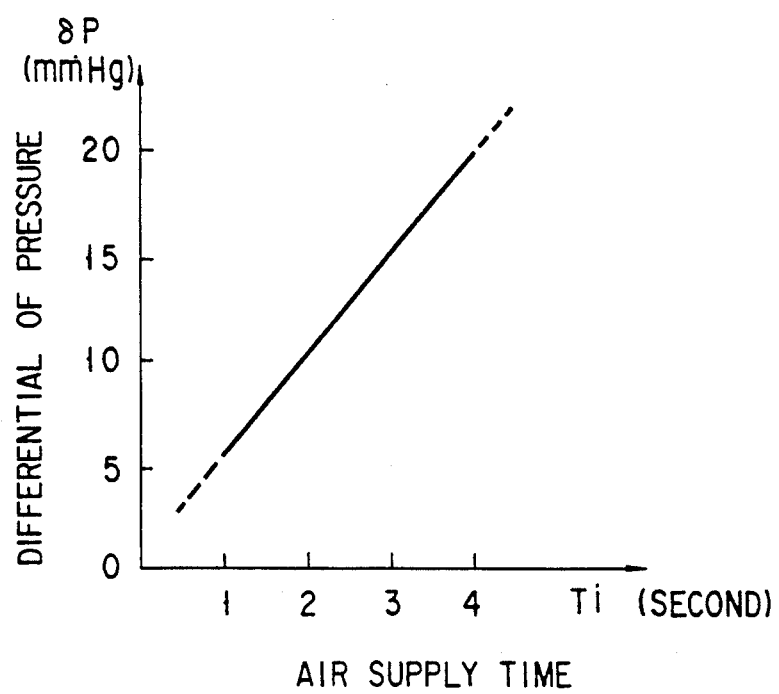
FIG. 3 is a graph showing the relation of differential pressure $\delta P$ relative to gas insufflating time Ti, said differential pressure being a value representing the difference between the intended pressure and a pressure in the body cavity measured in fact.

Some embodiments of the present invention will be described in detail with reference to the accompanying drawings. FIGS. 1 through 3 show the insufflation apparatus 1 according to an embodiment of the present invention. It is connected to a bomb unit 3, which serves as a gas supply source, enabling $CO_2$ gas filled in the bomb unit 3 to be insufflated into a cavity of the human body through a insufflation pipe 49. It is connected to this an insufflation pipe 49 through a tube 47 which is connected to a gas supply connector 45.

The bomb unit 3 comprises two gas bombs 3a and 3b. These two gas bombs 3a and 3b are located upstream of a first decompression means 6 in the insufflation apparatus 1 and connected to each other through a forked connection tube 10. Check valves 4 are arranged between the gas bomb 3a and the connection tube 10 and between the gas bomb 3b and the connection tube 10, respectively. Even if either of the gas bombs 3a and 3b is made empty and this empty gas bomb is removed from the apparatus 1, the leakage of $CO_2$ gas can be prevented by its corresponding check valve 4.

The connection tube 10 includes a bomb pressure sensor 5, which can detect the pressure of each of the gas bombs 3a and 3b and display the amount of gas in each of them.

The first decompression means 6 is connected to a second one 7 through an internal pipe 12. $CO_2$ gas of about 50 bars, maximum, sealed in the bomb unit 3 can be thus decompressed to about 3 bars by the first decompression means 6 and about 50-200 mmHg by the second one 7.

A relief valve 8 is attached to the internal pipe 12 between the first 6 and the second decompression means 7. This relief valve 8 serves as a safety one for releasing excessive gas into the air not to excessively add pressure to the second decompression means 7 when the first one 6 gets out of order and the pressure of gas decompressed by it becomes higher than 3 bars.

The internal pipe 12 for introducing $CO_2$ gas downstream the second decompression means 7 branches to two pipes 14a and 14b through a three-way electromagnetic valve 20. The pipe 14a further branches to two pipes 16a and 16b through a three-way electromagnetic valve 21 and these two pipes 16a and 16b serve to adjust the flow rate of $CO_2$ gas flowing through them. The pipe 16b has a differential pressure sensor 33 which serves as a first flow meter and by which $CO_2$ gas fed from the second decompression means 7 can be adjusted to a flow rate of about 16 lits/min. The pipe 16a has a first flow rate adjuster (or orifice) 30 and a differential pressure sensor 31 which serves as a second flow meter, and $CO_2$ gas fed from the second decompression means 7 can be therefore adjusted to a flow rate of about 8 lits/min by these first flow rate adjuster 30 and differential pressure sensor 31.

The pipe 16a further branches to two pipes 18a and 18b through a three-way electromagnetic valve 22 and these pipes 18a and 18b serve as flow rate adjuster pipe passages. The pipe 18a has a second flow rate adjuster (or orifice) 32 by which $CO_2$ gas fed through the three-way electromagnetic valve 22 can be adjusted to a flow rate of about 1 lit/min. $CO_2$ gas flowing from the pipe 16a into the pipe 18a via the three-way electromagnetic valve 22 is therefore adjusted to 8 lits/min by the first flow rate adjuster 30 and then 1 lit/min by the second flow rate adjuster 32. $CO_2$ gas flowing from the pipe 16a into the pipe 18b via the three-way electromagnetic valve 22 is fed while keeping its flow rate (of about 8 lits/min) which has been adjusted by the first flow rate adjuster 30.

The pipes 16b, 18a and 18b are again combined with one another on the downstream side and connected to a gas supply pipe 19 through a switch valve 25 which serves as a three-way electromagnetic valve. The gas supply pipe 19 is connected to a gas supply connector (not shown). When the switch valve 25 is powered, one of the pipes 16b, 18a and 18b is connected to the gas supply pipe 19. When it is not powered, the gas supply pipe 19 is connected to a pressure switch 40.

The other pipe 14b branching from the internal pipe 12 is connected to the gas supply pipe 19 downstream the switch valve 25. The pipe 14b has two two-way electromagnetic valves 23 and 24. An intermediate tank 34 provided with a pressure sensor 35 is arranged between the two-way electromagnetic valves 23 and 24. The pressure sensor 35 and the two-way electromagnetic valves 23, 24 are electrically connected to a body cavity pressure measuring unit 42, which measures the pressure of the body cavity via the pressure sensor 35 and the two-way electromagnetic valves 23, 24. The unit 42 is electrically connected to a pressure setting section 48 via an arithmetical unit 46 and the pressure setting section 48 serves to set an intended pressure in the body cavity. The arithmetic unit 46 is connected to a control unit 44 which is electrically connected to the switch valve 25 and it can calculate the difference of a pressure value measured by the body cavity pressure measuring unit 42 relative to the pressure value set by the pressure setting section 48. As will be described later, the control unit 44 can switch those timings at which the switch valve 25 is opened and closed on the basis of values calculated by the arithmetical unit 46.

Although not shown, the electromagnetic valves 20, 21, 22 and the pressure sensor 40 are electrically connected to the control unit 44.

It will be described how the insufflation apparatus 1 having the above-described arrangement is operated. At the initial stage of operation, $CO_2$ gas is fed, for safety, at a low flow rate of 1 lit/min, for example, through the insufflation apparatus 1 until it is confirmed whether or not the insufflation pipe 49 connected to the insufflation apparatus 1 is correctly inserted into the body cavity. This initial gas supply operation can be achieved when the operator sets the flow rate at 1 lit/min or selects a mode previously set at the lowest speed. The control unit 44 therefore switches the three-way electromagnetic valves 20, 21 and 22 so as to enable the internal pipe 12, the pipe 16a having the first flow rate adjuster 30, and the pipe 18a having the second flow rate adjuster 32 to be communicated with one another, and it also powers the switch valve 25 to cause the pipe 18a to be connected to the gas supply pipe 19.

When gas supply is done in this manner at the flow rate of 1 lit/min for a certain time period, the control unit 44 stops the supply of power to the switch valve 25 to disconnect the pipes 16b, 18a and 18b from the gas supply pipe 19. The pressure in the body cavity is then measured by the pressure sensor 35 attached to the pipe 14b which is communicated with the gas supply pipe 19. The gas supply pipe 19 is connected this time to the pressure switch 40 through the switch valve 25.

As will be later described in detail (with reference to FIGS. 8 through 10), the electromagnetic valve 23 is opened while the electromagnetic valve 24 is closed during this pressure measurement so as to fill the tank 34 with $CO_2$ gas till the pressure in it becomes about 50 mmHg. The electromagnetic valve 23 is then closed while opening the electromagnetic valve 24 and that change of the pressure in the tank 34 which is reduced as $CO_2$ gas is thus discharged from the tank 34 is measured by the unit 42 through the pressure sensor 35. The pressure in the body cavity is thus calculated.

This pressure measurement in the body cavity and the above-described low speed gas supply of 1 lit/min are alternately conducted while intermittently switching the electromagnetic valve 20 and opening and closing the switch valve 25.

A therapeutical treatment is then conducted in the gas-supplied body cavity while viewing an intended part in it through the endoscope, for example. During this therapeutical treatment, it sometimes happens that gas in the body cavity is leaked and that smoke is caused in the body cavity by laser and the electric surgical knife used. $CO_2$ gas is fed in these cases into the body cavity at high speed through the insufflation pipe 49, which is connected to the insufflation apparatus 1, so as to add the gas into the body cavity and remove the smoke from it.

This high speed gas supply operation can be achieved when the operator sets the flow rate at 16 lits/min or selects a mode previously set at the highest speed. The control unit 44, therefore, switches the three-way electromagnetic valve 21 to cause the internal pipe 12 and the pipe 16b to be communicated with each other and it also powers the switch valve 25 to cause the pipe 16b to be connected to the gas supply pipe 19.

Providing that the time Ti during which $CO_2$ gas is fed through the pipes 14a and 16b and the switch valve 25 is opened is represented by Ti (i=1, 2, 3, ---) and that the time t during which the pressure in the body cavity is measured through the pipe 14b while stopping the supply of $CO_2$ gas flowing through the pipes 14a and 16b and the switch valve 25 is closed is made equal to 500–1000 msec (or certain), these times Ti and t are controlled as shown in FIG. 2. This control can be practically achieved when the control unit 44 controls the times during which the switch valve 25 is opened and closed. In FIG. 2, ON- and OFF-operations of the switch valve 25 are plotted on the vertical axis while times during which the switch valve 25 is opened and closed are plotted on the horizontal axis.

It will be described how Ti changes as time goes by. When the operator inputs his intended value of pressure in the body cavity into the arithmetic unit 46 through the pressure setting section 48, the unit 44 calculates the difference δP of the intended pressure value relative to the practical pressure value in the body cavity measured by the unit 42. The control unit 44 then controls the switch valve 25 to be opened and closed in such a way that the gas supply time Ti becomes long when the differential pressure $\delta P$ is large and that Ti becomes relatively short when $\delta P$ is small. The relation of the gas supply time Ti relative to the differential pressure $\delta P$ is shown as an example in FIG. 3. When the differential pressure $\delta P$ becomes gradually smaller as the supply of gas is repeated, the gas supply time Ti is gradually made shorter. When the practical pressure in the body cavity is increased to 20%, 40%, 60% and 80% of the pressure set, for example, the gas supply time Ti is automatically reduced to 80%, 60%, 40% and 20% of the initial gas supply time. Synchronizing with the gas supply time Ti, the control unit 44 controls the times during which the switch valve 25 is opened and closed. When the gas supply and the measurement of pressure in the body cavity are alternately conducted while keeping the relation of the differential pressure $\delta P$ relative to the gas supply time Ti (i=1, 2, 3, ---), as described above, to make the pressure in the body cavity gradually nearer to the pressure set, the pressure in the body cavity can be prevented from exceeding the pressure set even if the gas supply is made at high speed.

The switching of the switch valve 25 is controlled, depending upon the gas supply time Ti and the pressure measuring time t, as described above. However, the value of pressure reduced by the second decompression means 7 is not exactly certain. In order to exactly control the amount of gas supplied, therefore, the gas supply time Ti can be corrected on the basis of values measured by the flow meters 31 and 33. More specifically, the control unit 44 changes, on the basis of values measured by the flow meters 31 and 33, the times during which the switch valve 25 is opened and closed to thereby exactly control the amount of gas supplied to the gas supply pipe 19.

When gas is to be fed at those flow rates which are excluded from about 1 lit/min and 16 lits/min set under the low and high speed modes or when gas is to be fed at a flow rate of 2–8 lits/min, for example, the three-way electromagnetic valves 20, 21 and 22 are switched to cause the internal pipe 12, the pipe 16a through which gas can be fed at a flow rate of 8 lits/min, maximum, and the pipe 18b to be communicated with one another. When gas is to be fed at a flow rate of 4 lits/min, for example, the time during which the switch valve 25 is opened is shortened half the time at the flow rate of 8 lits/min. When gas is to be fed at a flow rate of 9–16 lits/min, the three-way electromagnetic valves 20 and 21 are switched to cause the internal pipe 12 and the pipe 16b through which gas can be fed at the flow rate of 16 lits/min, maximum, to be communicated with each other. When gas is to be fed at the flow rate of 12 lits/min. the time during which the switch valve 25 is opened is shortened ¾ times the time at the flow rate of 16 lits/min.

As described above, the insufflation apparatus 1 according to the first embodiment of the present invention can calculate the difference of the pressure set relative to the practical pressure in the body cavity measured to thereby control the timings at which gas is fed. Although simpler in structure and operation, therefore, the apparatus enables a more speedy therapeutical treatment to be conducted at high speed gas supply and it also enables the gas supply to be achieved under a safer pressure which will never become excessive.

According to the insufflation apparatus 1, three kinds of flow rates can be obtained by three-way passage comprising the pipes 12, 16a and 18a (1 lit/min). the pipes 12, 16a and 18b (8 lits/min), and the pipes 12 and 16b (16 lits/min). Other flow rates can be obtained by controlling the times during which the switch valve 25 is opened and closed so as to change the flow rate per hour. In other words, the number of pipes used can be made smaller, the flow rate of $CO_2$ gas per hour can be selected from a wider range of values, the insufflation can be achieved under a safer pressure at low speed without excessively adding pressure into the body cavity, and more speedy therapeutical treatment can be conducted at high speed insufflation, when the times during which the switch valve 25 is opened and closed are changed and the three-way electromagnetic valves 20, 21 and 22 are changed over to select or combine one or more of the plural pipe passages which have different flow rates per hour. Further, any error of pressure set through the decompression means 7 and others can be corrected when the times during which the switch valve 25 is opened and closed is changed to exactly control the flow rate.

Still further, the speed of insufflation can be automatically changed from high to intermediate and low as the pressure in the body cavity increases, because the control unit 44 can control the electromagnetic valves 20, 21 and 22 to be opened and closed responsive to signals applied from the pressure sensor 35, by which the pressure in the body cavity is measured, so that the pipe passage through which $CO_2$ gas flows is changed over.

The flow rate of $CO_2$ gas insufflated is greatly changed by the passage resistance of the insufflation pipe 49 connected to the insufflation apparatus 1. When values of insufflation set are the same or pipe passages through which gas is insufflated are the same, the amount of gas insufflated through an insufflation pipe 49 whose passage resistance is larger becomes smaller as compared with that insufflated through another insufflation pipe 49 whose passage resistance is smaller. In these cases, therefore, the timings at which the switch valve 25 is opened and closed is controlled, as described below, while comparing the values measured by the flow meters 31 and 33 with the one measured by cavity pressure measuring unit 42.

Figure 4:
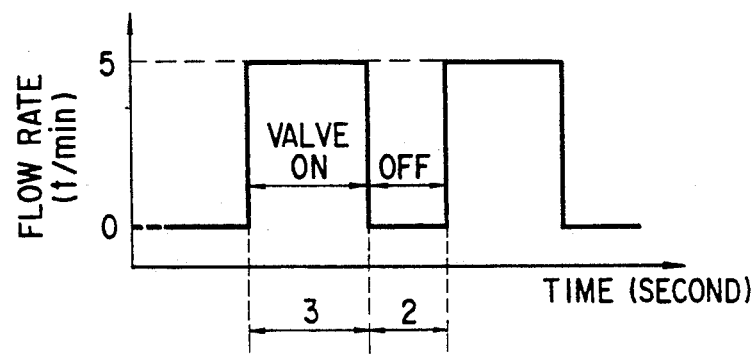
FIG. 4 is a time chart showing the relation of times during which the three-way electromagnetic valve is opened and closed relative to flow rates of gas insufflated in fact into the body cavity, said relation being obtained when the pressure of gas insufflated is set 3 lits/min and the gas insufflating pipe connected to the insufflation apparatus has a small passage resistance.
Figure 5:
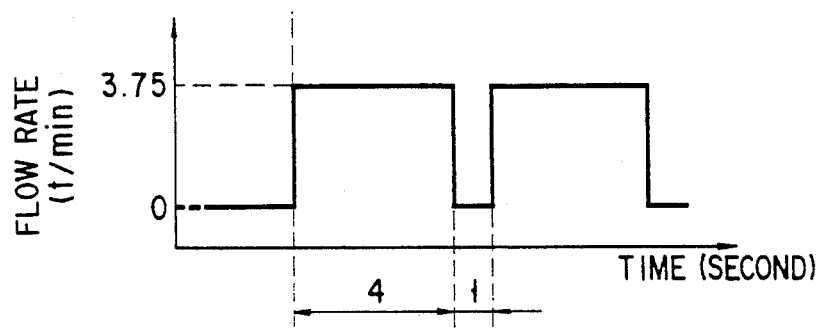
FIG. 5 is a time chart showing the relation of times during which the three-way electromagnetic valve is opened and closed relative to flow rates of gas insufflated in fact into the body cavity, said relation being obtained when the pressure of gas insufflated is set 3 lits/min and the gas insufflating pipe connected to the insufflation apparatus has a large passage resistance.

FIG. 4 is a time chart showing what relation the times during which the switch valve 25 is opened and closed have relative to the flow rate of gas practically insufflated into the body cavity when the flow rate of gas insufflated is set to 3 lits/min and the insufflation pipe 49 having smaller passage resistance is connected to the insufflation apparatus 1. FIG. 5 is a time chart obtained when the insufflation pipe 49 having larger passage resistance is connected to the insufflation apparatus 1 but at the set value of 3 lits/min. In both cases where the set value is 3 lits/min, the pipes 14a and 18b are selected.

It is assumed that the insufflation pipe 49 used has a small passage resistance, and that the amount of gas insufflated when the switch valve 25 is opened is 5 lits/min and one cycle of ON- and OFF-times of the switch valve 25 is 5 seconds, as shown in FIG. 4. If the ON-time of the switch valve 25 is 3 seconds and its OFF-time is 2 seconds under these conditions, the average flow rate becomes 3 lits/min, as previously set. The duty rate of these ON- and OFF-times of the switch valve 25 is determined by measuring the practical amount of gas insufflated by the flow meter 31 and applying this value measured to the arithmetic unit 46 through the cavity pressure measuring unit 42. The control unit 44 controls the switch valve 25 to be opened or closed responsive to a value calculated by the arithmetic unit 46.

When the insufflation pipe 49 has a large passage resistance, as shown in FIG. 5, the amount of gas insufflated is reduced from 5 lits/min in the case shown in FIG. 4 to 3.75 lits/min, for example. When the ON-time of the switch valve 25 as made 4 seconds and its OFF-time 1 second, therefore, the average flow rate becomes 3 lits/min, as previously set.

When the insufflation pipe 49 having an extremely large passage resistance is connected to the insufflation apparatus 1 and the practical amount of gas insufflated, therefore, becomes smaller than 3.3 lits/min, the OFF-time of the switch valve 25 becomes shorter than 0.5 seconds and this makes it impossible to measure the pressure in the body cavity as described above. Control in this case is made by either of two manners as described below.

One of them is to select the pipe 16b through which gas can be insufflated at 16 lits/min, maximum, so as to make small the resistance of internal pipe passage in the insufflation apparatus, so that the amount of gas insufflated can be made larger than 3.3 lits/min.

The other is to use a variable decompression means as the second decompression means 7 so as to change the pressure of gas insufflated. In a case where the value of pressure decompressed is usually set 50 mmHg, as described above, and the amount of gas insufflated is reduced smaller than 3.3 lits/min, the value of pressure decompressed by the second variable decompression means 7 through the control unit 44 is changed up to 200 mmHg so as to make the amount of gas insufflated larger than 3.3 lits/min. An electropneumatic proportional valve is used as variable decompression means in this case.

when the above-described two control manners are combined with each other, a wider range of measures can be employed relative to any changes of the passage resistance.

Figure 6:
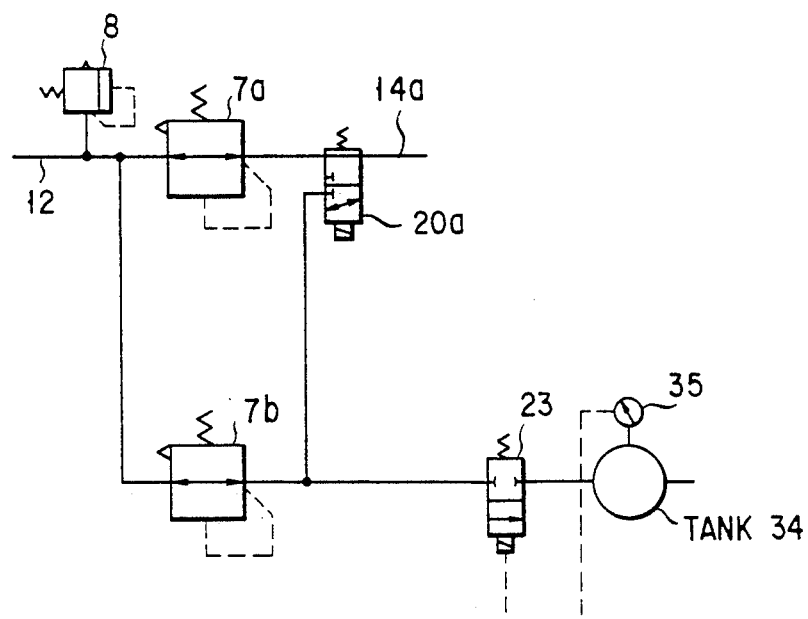
FIG. 6 is a circuit diagram showing a variation of the circuit arrangement peripheral to a second decompression means.

When either of two fixed decompression means 7a and 7b is selected by a three-way electromagnetic valve 20a, as shown in FIG. 6, the value of pressure decompressed on the secondary side can be changed. In the case shown in FIG. 6, the internal pipe 12 branches into two ways downstream the relief valve 8 and one of them is connected to the three-way electromagnetic valve 20a through the decompression means 7a in which the value of pressure decompressed is set 200 mmHg, while the other to the decompression means 7b in which the value of pressure decompressed is set 50 mmHg. The pipe passage downstream the decompression means 7b also branches into two ways and one of them is connected to the three-way electromagnetic valve 20a while the other to the tank 34 through the electromagnetic valve 23. The three-way electromagnetic valve 20a selectively connects either of the decompression means 7a and 7b to the pipe 14a. The arrangement of other components is the same as in the case shown in FIG. 1.

Using the components arranged as shown in FIG. 6, it will be described that pressure in the pipe passage to the pressure switch 40 is made smaller than the pressure by which the pressure switch 40 is made operative and that the operation of the pressure switch 40 caused by the passage resistance of the insufflation pipe 49 prevents the insufflating operation of the insufflation apparatus 1 from being stopped.

The pressure in the body cavity is measured at the time when the insufflation of gas is started. This measurement is made in the same manner as in the case shown in FIG. 1 and the measurement of passage resistance is also made at the same time.

Figure 7:
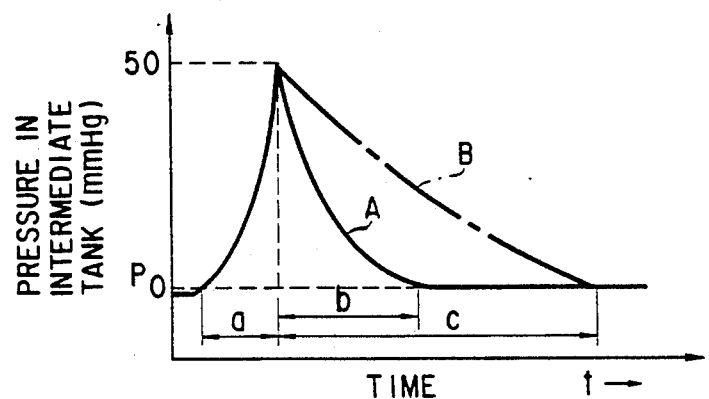
FIG. 7 is a graph showing the relation of the pressure in an intermediate tank relative to time.

FIG. 7 is a graph showing the relation of pressure in the intermediate tank 34 relative to time. A time period a in the graph represents that the tank 34 is filled with $CO_2$ gas while opening the two-way electromagnetic valve 23 and closing the two-way electromagnetic valve 24. The pressure in the tank 34 rises to the decompressed pressure value of 50 mmHg in this time period. When the pressure in the tank 34 reaches 50 mmHg and the two-way electromagnetic valve 23 is closed and the two-way electromagnetic valve 24 is opened, the pressure in the tank 34 falls to the pressure in the body cavity.

The falling characteristic of pressure in the tank 34 depends upon the passage resistance of the insufflation pipe 49 connected to the insufflation apparatus 1. When the insufflation pipe 49 having a small passage resistance is connected to the insufflation apparatus 1 (see a curve A in FIG. 7), the time during which the pressure in the tank 34 falls to the pressure in the body cavity becomes short (time period b) and when the insufflation pipe 49 having a large passage resistance is connected to the insufflation apparatus 1 (see a curve B in FIG. 7), the falling time becomes long (time period c). This characteristic can be confirmed by the arithmetic unit 46 through the cavity pressure measuring unit 42.

The passage resistance is measured in this manner during the measuring process of the pressure in the body cavity and the insufflating operation is then started. The control unit 44 selects in this case either of the decompression means 7a and 7b responsive to the value of passage resistance confirmed by the arithmetic unit 46. It will be described in detail how this selection is made.

When the insufflation pipe 49 whose passage resistance is small is connected to the insufflation apparatus 1, the control unit 44 selects the decompression means 7a responsive to the value of passage resistance confirmed by the arithmetic unit 46 and the pressure of gas insufflated is set to 200 mmHg. When the switch valve 25 is then powered, $CO_2$ gas is insufflated into the body cavity. Because the passage resistance of the insufflation pipe 49 connected to the insufflation apparatus 1 is small, the pressure of gas insufflated falls to about 40 mmHg through the switch valve 25. Even if the supply of power to the switch valve 25 is stopped after the gas insufflation and the pressure switch 40 is connected to the gas insufflating pipe 19, therefore, the pressure switch 40 is not made operative because the value of pressure set for the pressure switch 40 is 50 mmHg.

When the insufflation pipe 49 whose passage resistance is large as seen in the case of an insufflation needle is connected to the insufflation apparatus 1, the control unit 44 selects the decompression means 7b responsive to the value of passage resistance confirmed by the arithmetic unit 46 and the pressure of gas insufflated is set to 50 mmHg. (If the decompression means 7a is selected and the pressure of gas insufflated is set to 200 mmHg in this case without measuring the passage resistance during the measuring process of pressure in the body cavity, the pressure of gas insufflated is made about 150 mmHg through the switch valve 25 because the passage resistance of the insufflation pipe 49 is large. When the supply of power to the switch valve 25 is stopped, under this state, after the insufflation of gas and the pressure switch 40 is connected to the gas insufflating pipe 19, the pressure switch 40 is made operative to stop the gas insufflating operation of the insufflation apparatus 1). When the insufflation pipe 49 whose passage resistance is large is connected to the insufflation apparatus 1 as described above, the decompression means 7b is selected on the basis of the value of passage resistance previously measured and the pressure of gas insufflated is made smaller than 50 mmHg through the switch valve 25 to thereby prevent the pressure switch 40 from being wrongly operated.

When the insufflation pipe 49 whose passage resistance is large is connected to the insufflation apparatus 1, it is needed that the insufflation of gas is made careful at the initial stage. The insufflation of gas, therefore is made not at high speed but at low speed under the pressure of 50 mmHg. It may be arranged that the decompression means 7a and 7b are replaced by a variable decompression means such as the electropneumatic proportional valve and that the value of pressure decompressed by the variable decompression means (or the pressure of gas insufflated) is controlled by the control unit 44. According to the above described arrangement of components shown in FIG. 6, the effect of pressure remaining in the pipe passage and acting on the pressure switch 40 can be eliminated and the pressure switch 40 can be operated with a higher reliability.

Figure 8:
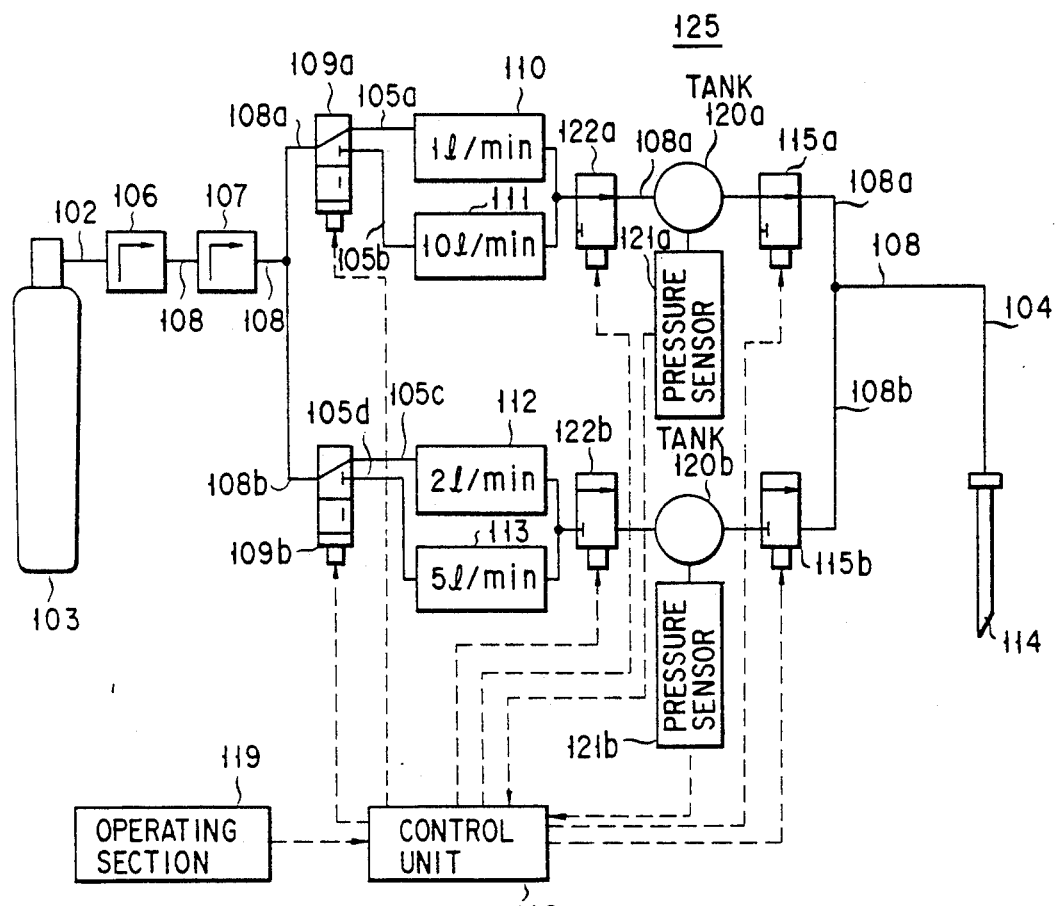
FIG. 8 is a circuit diagram showing the insufflation apparatus according to a second embodiment of the present invention.

FIG. 8 shows a second embodiment of the present invention. An insufflation apparatus 125 according to this embodiment is connected to a bomb 103 which serves as the gas supply source. $CO_2$ gas filled in the bomb 103 can be insufflated into the body cavity through an insufflation needle 114 which serves as the insufflation pipe.

The bomb 103 is connected to a first decompression means 106 in the insufflation apparatus 125 via a connection tube 102. The first decompression means 106 is connected to a second one 107 via an internal pipe 108. $CO_2$ gas of about 50 bars, maximum, filled in the bomb 103 is thus reduced to about 1-2 bars through the first decompression means 106 and to about 50-100 mmHg through the second decompression means 107.

The internal pipe 108 through which $CO_2$ gas is introduced downstream the second decompression means 107 branches midway into two ways. Connected midway one 108a of them through a three-way electromagnetic valve 109a, which is electrically connected to a control unit 118, are two pipes 105a and 105b which serve as flow rate adjusting passages arranged parallel to each other. More specifically, the first pipe 105a has a flow rate adjuster 110 by which the amount of gas insufflated is limited to 1 lit/min and it is connected to one outlet of the three-way electromagnetic valve 109a, while the second pipe 105b has a flow rate adjuster 111 by which the amount of gas insufflated is limited to 10 lits/min and it is connected to another outlet of the electromagnetic valve 109a. The first and second pipes 105a and 105b are combined with each other downstream the flow rate adjusters 110 and 111 and again connected to the pipe 108a through a stopper valve 122a which is electrically connected to the control unit 118. An intermediate tank 120a and a switch valve 115a are connected in this order to the pipe 108a downstream the stopper valve 122a. The switch valve 115a is also electrically connected to the control unit 118. The intermediate tank 120a has a pressure sensor 121a electrically connected to the control unit 118.

Two pipes 105c and 105d which serve as flow rate adjusting passages arranged parallel to each other are connected midway the other pipe 108b, which branches from the internal pipe 108, through a three-way electromagnetic valve 109b electrically connected to the control unit 118. More specifically, the third pipe 105c has a flow rate adjuster 112 by which the amount of gas insufflated is limited to 2 lits/min and it is connected to an outlet of the three-way electromagnetic valve 109b, while the fourth pipe 105d has a flow rate adjuster 113 by which the amount of gas insufflated is limited to 5 lits/min and it is connected to another outlet of the three-way electromagnetic valve 109b. The third and fourth pipes 105c and 105d are combined with each other downstream the flow rate adjusters 112 and 113 and again connected to the pipe 108b through a stopper valve 122b electrically connected to the control unit 118. An intermediate tank 120b and a switch valve 115b are connected in this order to the pipe 109b downstream the stopper valve 122b. The switch valve 115b is also electrically connected to the control unit 118. The intermediate tank 120b has a pressure sensor 121b electrically connected to the control unit 118.

The switch valves 115a and 115b serve as ordinary ones for controlling the communication of the pipes 105 (105a–105d) and 108 and they also serve as relief ones for releasing $CO_2$ gas, which is in the pipe passage to the body cavity, into the air when the pressure in the body cavity exceeds a certain pressure (or 50 mmHg, for example).

The forked pipes 108a and 108b are combined with each other downstream the switch valves 115a and 115b to again form the internal pipe 108, through which $CO_2$ gas fed through the flow rate adjusting pipes 105a, 105b, 105c and 105d can be insufflated downstream. The flow rate adjusters 110, 111,112 and 113 comprise orifice pipes and speed controllers (or elements whose sections can be adjusted).

A connection tube 104 which is connected to the insufflation needle 114 is connected to the downstream end of the internal pipe 108. $CO_2$ gas fed through the internal pipe 108 is thus insufflated into the insufflation needle 114 through the connection tube 104. An operating section 119 is connected to the control unit 118 and when the pressure and amount of gas insufflated are set and inputted to the control unit 118 through the operating section 119, the control unit 118 can control operations of the electromagnetic valves 109a, 109b, 115a, 115b and others responsive to these values thus inputted.

It will be described how the insufflation apparatus 125 arranged as described above is operated. The safe gas-insufflating operation which is conducted at a low flow rate (or 1 lit/min) at the initial stage is achieved, as seen in the case of the first embodiment, when the operator sets the flow rate at 1 lit/min and selects a mode of the lowest speed, for example, through the operating section 119. The control unit 118 thus switches three-way electromagnetic valve 109a to communicate the internal pipe 108 with the first pipe 105a, which has the flow rate adjuster 110, while opening the switch valves 115a, 122a and closing the switch valve 115b.

when the insufflation of gas is made for a certain time according to the above-described safe gas-insufflating operation, the control unit 118 causes the switch valve 115a to be closed and the stopper valve 122b to be opened, thereby allowing $CO_2$ gas to be introduced into the intermediate tank 120b. The stopper valve 122b is kept open until pressure $P_1$ in the intermediate tank 120b becomes equal to 30 mmHg.

Responsive to pressure signal applied from the pressure sensor 121b, the control unit 118 detects that the pressure $P_1$ in the intermediate tank 120b has become equal to 30 mmHg and it therefore causes the stopper valve 122b to be closed and the switch valve 115b to be opened. When any differential pressure exists this time between pressures in the intermediate tank 120b and body cavity, $CO_2$ gas in the intermediate tank 120b flows into the body cavity. The pressure in the intermediate tank 120b is measured three times at a certain time interval during this gas insufflating process. When the difference between pressures in the intermediate tank 120b and body cavity is large, the pressure in the intermediate tank 120 drops instantly, as shown in FIG. 9 ($P_0$ represents balanced pressure in this case). When the insufflation of gas is then repeated according to the same operation and the difference between pressures in the intermediate tank 120b and body cavity becomes small, the drop of the pressure in the intermediate tank 120b becomes gentle and using pressure values measured three times at points a, b and c ($P_a$ denotes pressure at point a, $P_b$ pressure at point b and $P_c$ pressure at point c), pressure $P_2$ in the body cavity is indirectly calculated by the following equations (1) and (2).

$$P2 = \frac{P_b - P_a \times X}{1 - X} \quad (1)$$

$$X = \frac{P_b - P_c}{P_a - P_b} \quad (2)$$

This arithmetic calculation of the pressure $P_2$ in the body cavity is made by the control unit 118. While conducting this measurement of the pressure $P_2$ in the body cavity, the insufflation apparatus 125 insufflates $CO_2$ gas into the body cavity until the pressure in it becomes equal to the value set. The control unit 118 calculates, in this case, differences between the pressure set by the operating section and pressures practically measured as described above by the pressure sensor 121b (or 121a). According to these differences, the control unit 118 controls the electromagnetic valves 109a, 109b, 122a, 122b, 115a and 115b, as seen in the case of the first embodiment, to automatically switch the pipe passage through which $CO_2$ gas flows and change the timings at which the switch valves 115a and 115b are opened and closed.

The flow rate of gas insufflated and others during the gas insufflating process are set as follows. In order to conduct the high speed insufflation, for example, the operator sets the flow rate at 15 lits/min and selects a mode previously set at the highest speed through the operating section. The control unit 118, therefore, switches the three-way electromagnetic valve 109a to communicate the internal pipe 108 with the second pipe 105b which has the flow rate adjuster 111. At the same time, it also switches the three-way electromagnetic valve 109b to communicate the internal pipe 108 with the fourth pipe 105d which has the flow rate adjuster 113. Therefore, $CO_2$ gas of 15 lits/min resulting from $CO_2$ gas of 10 lits/min insufflated through the second pipe 105b and $CO_2$ gas of 5 lits/min insufflated through the fourth pipe 105d is insufflated into the body cavity.

When the ways in which the three-way electromagnetic valves 109a and 109b are switched and the opening and closing of the switch valves 115a and 115b are combined with one another in this manner, eight kinds of flow rates including 1, 2, 1+2=3, 5, 1+5=6, 10, 10+2=12, and 10+5=15 can be obtained although the number of pipe passages is only four (105a, 105b, 105c and 105d).

As described above, the insufflation apparatus 125 can calculate differences between the pressure set and pressures practically measured to control the gas insufflating timings (or timings at which the switch valves 115a and 115b are opened and closed). Although simpler in structure and operation, therefore, it enables a more speedy therapeutical treatment to be conducted at the high speed insufflation and the insufflation of gas to be achieved under a safer pressure without excessively adding pressure into the body cavity.

Further, the insufflation apparatus 125 enables eight kinds of flow rate to be achieved through four pipe passages, but in order to obtain other flow rates which are not included in the eight ones, the opening and closing the the switch valves 115a and 115b are controlled, as seen in the case of the first embodiment, to change the flow rate per a time unit. According to the insufflation apparatus 125, therefore, the opening and closing times of the switch valves 115a and 115b are changed and the three-way electromagnetic valves 109a, 109b, 122a, 122b, 115a and 115b are switched to optionally select and combine one or more of the plural pipe passages (105a–105d) whose flow rates per a time unit are different. As the result, a wider range of flow rates per a time unit at which $CO_2$ gas is insufflated into the body cavity can be set although smallest in the number of pipe passages selected and combined. At the same time, the insufflation of gas can be achieved under a safer pressure and at so low a speed as not to excessively add pressure into the body cavity and a more speedy therapeutical treatment can be conducted at high speed insufflation. In addition, the insufflation apparatus 125 changes the opening and closing times of the switch valves 115a and 115b to exactly control the flow rate. This enables any error of the pressure set through the decompression means 107 to be corrected.

Still further, the insufflation apparatus 125 enables the control unit 118 to control the opening and closing of the electromagnetic valves 109a, 109b, 122a, 122b, 115a and 115b so as to automatically change the pipe passage through which $CO_2$ gas flows, as seen in the case of the first embodiment. The gas insufflating speed can be thus changed from high to intermediate and further to low as the pressure in the body cavity rises.

The flow rate is set at 1, 2, 5 and 10 lits/min through the flow rate adjusters 110, 111, 112 and 113 in the case of this second embodiment, but it is not limited to these values and the number of pipe passages selected is not limited to four either.

FIG. 11 shows a third embodiment of the present invention. An insufflation apparatus 126 according to this embodiment is different from the second embodiment only in the system for measuring the pressure in the body cavity and the arrangement of its other components is the same as that in the case of the second embodiment. The same components as those in the second embodiment will be therefore denoted by same reference numerals and description on these components will be omitted.

First and second pipes 105a and 105b are combined with each other downstream the flow rate adjusters 110 and 111 and again connected to the pipe 108 through the switch valve 115a which is electrically connected to the control unit 118. A downstream end of the internal pipe 108 is forked and the connection tube 104 which is connected to the insufflation needle 114 is connected to an end of one of the forked pipe. $CO_2$ gas fed through the internal pipe 108 is thus insufflated into the insufflation needle 114 through the connection tube 104.

A pressure sensor 117 which is electrically connected to the control unit 118 is attached to the other 116 of the forked pipe 108 and pressure in the pipe 116 which is communicated with the body cavity is measured by the pressure sensor 117.

The control unit 118 calculates differences between the pressure set through the operating section 119 and those in the body cavity practically measured by the pressure sensor 117. According to these values, the electromagnetic valves 109a, 109b, 122a, 122b, 115a and 115b are controlled, as seen in the case of the first embodiment, to automatically change the pipe passage through which $CO_2$ gas flows and also change the timings at which the switch valves 115a and 115b are opened and closed. In the case of the insufflation apparatus 126, therefore, same operational merits as those achieved by the second embodiment can be obtained.

FIG. 12 shows the insufflation apparatus 127 according to a fourth embodiment of the present invention. According to the insufflation apparatus 127, five switch valves 123a, 123b, 123c, 123d and 123e are connected parallel to one another between a variable decompression means 128 and the connection tube 104. The variable decompression means 128 is electrically connected to a control unit 129 and it can produce any outlet gas pressure proportional to electric signals applied from the control unit 129.

Switch valves 123a, 123b, 123c, 123d and 123e are electrically connected to the control unit 129. Each of them has the same effective sectional area and a substantially the same flow rate can be obtained under the same pressure through each of them. The arrangement of other components is the same as in the case of the third embodiment shown in FIG. 11 and description on these same components will be therefore omitted.

In the case of the insufflation apparatus 127, therefore, the control unit 129 controls the opening and closing of each of the switch valves 123a, 123b, 123c, 123d and 123e and also changes the outlet gas pressure of the variable decompression means 128. The flow rate of gas insufflated into the body cavity can be thus changed.

When the pressure of the variable decompression means 128 is made certain (or 50 mmHg, for example) and one switch valve is opened and closed at a certain interval (the flow rate of gas insufflated is made 2 lits/min, for example, in this case), as shown at the upper portion of FIG. 13, the pressure in the body cavity changes as shown at the lower portion of FIG. 13. Namely, a relatively long time is needed until the pressure in the body cavity reaches a value P (or 10 mmHg, for example) set, and in this case where the flow rate of gas insufflated is made relatively large or 2 lits/min, the overshooting y of pressure becomes large near the value P set. In a case where gas is leaked from the body cavity (see x in FIG. 13), the time needed to add gas into the body cavity becomes relatively long because the flow rate of gas (2 lits/min) insufflated is kept unchanged.

However, this problem can be solved when the flow rate of gas insufflated is changed through the components arrangement shown in FIG. 12. The pressure of the variable decompression means 128 is changed within a range of 50–200 mmHg, for example, and the number of the switch valves 123a–123e opened and closed is adjusted optional. When the flow rate of gas insufflated is thus changed to obtain the smallest flow rate near the pressure value P set (only one electromagnetic valve is opened and the outlet pressure of the decompression means is made 50 mmHg, for example), as shown in FIG. 14, the pressure in the body cavity can be made equal to the value set for a shorter time and the overshooting of pressure in the vicinity of the pressure value P set can be made minimum.

As shown at the upper portion of FIG. 14, the flow rate is set high at the start of the insufflation by opening all of the switch valves 123a–123e and setting the outlet pressure of the variable decompression means 128 at 200 mmHg. The number of the switch valves 123a–123e opened is then decreased and the outlet pressure of the variable decompression means 128 is lowered (or only one of the switch valves is opened and the outlet pressure of the variable decompression means is lowered to 50 mmHg, for example) to gradually reduce the flow rate of gas insufflated and obtain the smallest flow rate near the pressure value P. The control unit 129 controls the number of the switch valves 123a–123e opened and the outlet pressure of the variable decompression means, responsive to the information obtained from the pressure sensor 117 and relating to the pressure in the body cavity.

In the case where gas is leaked from the body cavity and the pressure in it falls suddenly (see X in FIG. 14), the control unit 129 controls, on the basis of signals applied from the pressure sensor 117, in such a way that the difference between the pressure in the body cavity at the time of this pressure fall and the pressure set is calculated, that the number of the switch valves 123a–123e opened and the outlet pressure of the variable decompression means 128 are determined depending upon this differential pressure calculated, and that an appropriate amount of gas is added into the body cavity. Therefore, the gas can be quickly added into the body cavity under safe pressure while making the overshooting of pressure minimum.

The flow rates plotted on the vertical axis at the upper portion of FIG. 14 depend upon the number of the switch valves 123a–123e opened and the outlet pressure of the variable decompression means 128 set. The horizontal axis at the upper portion of FIG. 14 represents time periods during which the switch valves 123a–123e are opened. Each of rectangular areas defined by flow rates on the vertical axis and time periods on the horizontal axis denotes an accumulated amount of gas insufflated into the body cavity.

When the same one of the switch valves 123a–123e is continuously driven, its life becomes shorter, as compared with those of the others. When only one of them is to be opened, therefore, they are successively changed from 123a to 123b, then to 123c, still then to 123d, and still then to 123e every operation, as shown in a time chart in FIG. 15. When two of them are to be opened, they are successively changed from a pair of 123a and 123b to another pair of 123c and 123d and then to a further pair of 123e and 123a every operation, etc., as shown in a time chart in FIG. 16. Even when the number of them to be opened is three or four, the same changeover of them is conducted.

This operation of equally driving all of the switch valves is achieved according to software and it will be described referring to a flow chart in FIG. 17.

When the gas insufflating operation is started at a stage 132, conditions to be set are made ready for being inputted at a stage 134. When an initial flow rate of gas (15 lits/min, for example) insufflated and a pressure (10 mmHg, for example) are set, the number of switch valves opened is automatically selected at a stage 136 and their opening is then started at a stage 138.

When their opening is not finished at a stage 140, the pressure in the body cavity is measured at a stage 142. When this pressure measured does not exceed the pressure set, the process is returned to the stage 136. As the difference between the pressure measured and the pressure set becomes smaller, the number of the switch valves opened is automatically reduced. Operations of the switch valves shown in time charts in FIGS. 15 and 16 are conducted at the stage 138, depending upon the number of them opened.

When the pressure in the body cavity reaches the pressure set, the opening of the switch valves is stopped at a stage 144. When their operation is not finished at a stage 146, the pressure in the body cavity is again measured at a stage 148. When this pressure measured is made smaller than the pressure set, the process is returned to the stage 136 and the opening of the switch valves is started. When a power switch (not shown) is turned off or a stop switch is turned on at the stages 140 and 146, the whole of the process is finished.

This operation or process of equally driving all of the switch valves 123a–123e can also be achieved by a pulse counter 154 shown in FIG. 18. Each of the switch valves 123a, 123b, 123c, 123d and 123e is electrically connected to the pulse counter 154, which is connected to a control unit 152.

The pulse counter 154 counts how many times each of the switch valves is operated and it applies the counted number of each of them to the control unit 152, which controls all of them to be equally operated on the basis of their counted number.

As described above, the flow rate of gas insufflated is changed by controlling the number of the switch valves 123a–123e opened, the time periods during which they are opened, and the outlet pressure of the variable decompression means 128. However, it may be changed by a mass flow controller 164 shown in FIG. 19.

The mass flow controller 164 is located on a gas supply line which connects the second decompression means 107 to the connection tube 104, and its outlet flow rate is changed by a control unit 162. It includes therein a control valve which serves to control the flow rate of gas insufflated. This control valve is controlled by set voltage applied from an external unit such as the potentiometer so as to allow gas to be insufflated at a flow rate set.

In the case of this components arrangement shown in FIG. 19, a signal representing the value of flow rate set through the operating section 119 is applied from the control unit 164 to the mass flow controller 164. Therefore, automatic control can be achieved in such a way that the insufflation is initially conducted at a high speed of 15 lits/min, for example, and that while reducing its speed, it is then conducted at a low speed of 1 lit/min when the pressure measured is in the vicinity of the pressure set. The mass flow controller 164 can control the flow rate per a time unit in analog manner, responsive to signals applied. According to the components arrangement shown in FIG. 19, it is simpler in structure but it can change the flow rate successively. This enables a more exact insufflation control to be achieved while keeping pressure change smaller.

An insufflation apparatus having two pressure sensors capable of measuring static and dynamic pressures in the body cavity and also capable of being changed over from one to the other will be described.

The insufflation apparatus 201 shown in FIG. 20 comprises a trocar 226 which serves as the insufflation pipe inserted into the body cavity through the skin of the human body, and an insufflation unit 203 which serves to control the pressure of gas insufflated. In the case of this insufflation apparatus 201, gas (or $CO_2$ gas, for example) supplied from a gas bomb 202 which serves as the gas supply source is insufflated into the body cavity through a front tip of the trocar 226 which is stuck into the body cavity.

The gas bomb 202 is connected to a decompressing section 204 of the insufflation apparatus 203 via a connection tube 214 and the decompressing section 204 has a first decompressing valve (not shown). The decompressing section 204 is connected to a pressure/flow rate control section 206 through an internal pipe 216. The pressure/flow rate control section 206 has a second decompressing valve (not shown) and it can control the pressure and flow rate of gas insufflated into the body cavity. 10 The trocar 226 is connected to the pressure/flow rate control section 206 via a gas insufflating pipe 218. The trocar 226 and the pipe 218 are connected to each other through a connector 229. The connectors 229 for connecting the pipe 218 and an electric line 228, which will be described later, to the trocar 226 are shown as different ones in FIG. 20 but this is intended to exaggerate that the gas insufflating line 218 and the electric line 228 are quite different or arranged independent of the other in a connector cable 221 (see FIG. 21). Therefore, the connectors 229 are formed in fact as a single unit.

The gas insufflating pipe 218 is communicated with the body cavity through the trocar 226 which is stuck into the body cavity. A pressure sensor 220 is attached midway the pipe 218 to measure the pressure in the pipe 218.

Another pressure sensor 222 for measuring the static pressure in the body cavity is attached to that front end portion of the trocar 226 which is not contacted with gas insufflated into the body cavity through the trocar 226 and which is stuck into the body cavity at the time when gas is to be insufflated into the body cavity. This front end portion of the trocar 226 will be hereinafter referred to as the stuck portion. The pressure sensor 222 is connected to a sensor confirming section 210 and an input terminal of a sensor changeover switch 224 in the insufflation apparatus 203 via the connector 229 and electric line 228. The output side of the pressure sensor 220 is connected to another input terminal of the sensor changeover switch 224. An output terminal of the sensor changeover switch 224 is connected to a pressure control section 212, which is connected to the pressure/flow rate control section 206. A feedback control circuit is thus formed.

The sensor confirming section 210 is connected to changeover section 208. The changeover section 208 has signal lines 205 and 207. Signals for changing the pressure and flow rate set to insufflate gas into the body cavity, depending upon the pressure sensors 220 and 222, are applied to the pressure/flow rate control section 206 through the signal line 205. Signals for changing one of the sensors 220 and 222 to the other are applied to the sensor changeover switch 224 through the signal line 207.

As shown in FIG. 21, the pressure sensor 222 is embedded in the stuck portion of the trocar 226. The pressure sensing area of the pressure sensor 222 is exposed outside through an opening 242 which is formed in the outer face of the stuck portion of the trocar 226, as shown enlarged in FIG. 22.

The pressure sensor 222 is connected to an internal connector 232, which serves as a contact in a connector receptacle 241 of the trocar 226, through an electric wire 230. An internal connector 234 which serves as a contact connected to the electric line 228 is provided in the connector 229. When the connector 229 is connected to the connector receptacle 241 of the trocar 226, the internal connectors 232 and 234 are electrically connected to teach other. The pressure sensor 222 is thus electrically connected to the insufflation unit 203 via the electric wire 228 in the connector cable 221 and the trocar 226 is also communicated with the gas insufflating pipe 218. When the connector 229 is to be connected to the connector receptacle 241, the former is pushed onto the latter to fit the former's tapered engaging portion 238 round the latter's tapered engaged portion 240.

Figure 23:
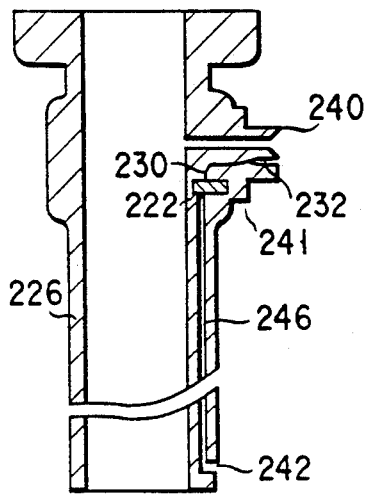
FIG. 23 is a sectional view showing a variation of that portion of the gas insufflating pipe (or trocar) where the trocar is connected to the insufflation unit.

As shown in FIG. 23, the pressure sensor 222 may be located adjacent to the connector receptacle 241 of the trocar 226. A hole 246 through which the pressure in the body cavity can be transmitted to the pressure sensor 222 through the opening 242 is provided in the trocar 226 in this case. When the pressure sensor 222 is arranged in this manner, the stuck portion of the trocar 226 is not needed to have any space for receiving the pressure sensor 222. Therefore, it can be made slenderer to have a smaller diameter and this reduces the burden of a patient. The diameter of the hole 246 may be made extremely small if the pressure in the body cavity can be transmitted to the pressure sensor 222 through the hole 246. In other words, the hole 246 is not needed to make its passage resistance small.

Figure 24:
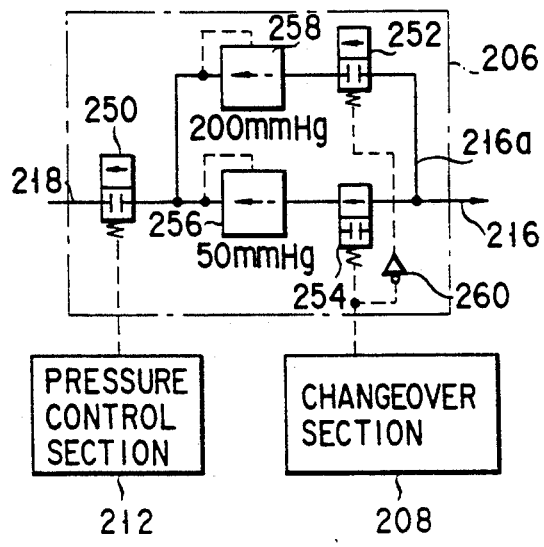
FIG. 24 is a circuit diagram showing a pressure/flow rate control section.

The pressure/flow rate control section 206 of the insufflation apparatus 203 will be described referring to FIG. 24.

A first electromagnetic valve 254 is arranged in the pressure/flow rate control section 206. The internal pipe 216 which is connected to the decompressing section 204 is connected to the first electromagnetic valve 254. The internal pipe 216 branches upstream the first electromagnetic valve 254 and its forked pipe 216a is connected to a second electromagnetic valve 252 in the pressure/flow rate control section 206. the first electromagnetic valve 254 is electrically connected to the changeover section 208 and the second one 252 is also electrically connected to it through an inverter 260. Either of the first and second electromagnetic valves 254 and 252 is opened responsive to changeover signals applied from the changeover section 208.

A decompression means 256 which serves to decompress the pressure of gas to 50 mmHg is connected to the downstream side of the first electromagnetic valve 254 through the internal pipe 216. Another decompression means 258 which serves to decompress the pressure of gas to 200 mmHg is connected to the downstream side of the second electromagnetic valve 252 via the internal pipe 216a. The pipes 216 and 216a extending from the decompression means 256 and 258, respectively, are combined with each other and a third electromagnetic valve 250 which serves to control gas flowing from the internal pipe 216 to the gas insufflating pipe 218 is arranged downstream the point at which the pipes 216 and 216a are jointed. The third electromagnetic valve 250 is electrically connected to the pressure control section 212 and its opening and closing are controlled by electric signals applied from the pressure control section 212.

The sensor confirming section 210 and its peripheral circuit will be described with reference to FIG. 25.

Figure 25:
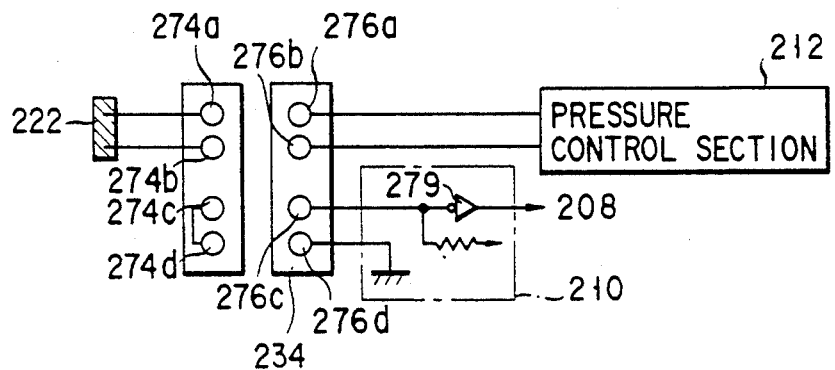
FIG. 25 is a circuit diagram showing a connector by which the gas insufflating pipe (or trocar) is connected to the insufflation unit.

As shown in FIG. 25, the pressure sensor 222 is connected to the pressure control section 212 and the sensor confirming section 210 through the internal connector 232 in the connector receptacle 241 of the trocar 226 and through the internal connector 234 in the connector 229 of the connector cable 221 connected to the insufflation unit 203.

Each of the internal connectors 232 and 234 has four terminals. Two 274c and 274d of four terminals of the internal connector 232 are short-circuited to each other. These two terminals 274c and 274d are connected to their corresponding terminals 276c and 276d of the internal connector 234 when the connectors 232 and 234 are connected to each other. The terminal 276c is connected to the changeover section 208 via an inverter 276 in the sensor confirming section 210 and the terminal 276d to the ground.

The other two terminals 274a and 274b of the internal connector 232 are connected to their corresponding terminals 276a and 276b of the internal connector 234 when these connectors are connected to each other. The pressure sensor 222 is thus connected to the pressure control section 212.

When the internal connectors 232 and 234 are connected to each other, therefore, the input of the inverter 279 of the sensor confirming section 210 is short-circuited to the ground. Outputs of the inverter 279 thus become high in level, thereby enabling the connection of the pressure sensor 222 relative to the insufflation unit 203 to be confirmed.

Figure 26:
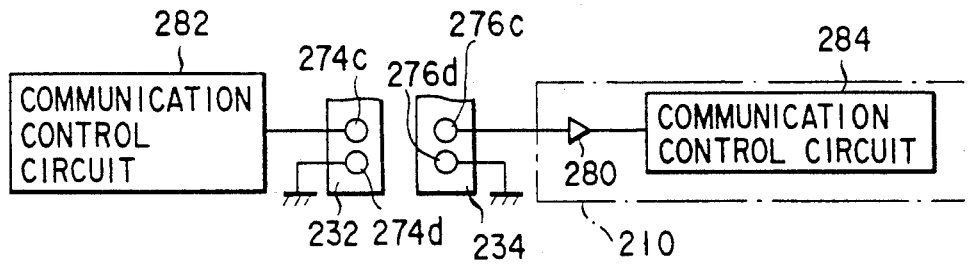
FIG. 26 is a circuit diagram showing a variation of the components arrangement shown in FIG. 25.

FIGS. 26 through 28 show other manners of connecting the pressure sensor 222, sensor confirming section 210 and pressure control section 212 to one another.

In FIG. 26, two terminals 274c and 274d of the internal connector 232 are not short-circuited to each other but the terminal 274c is connected to a communication control circuit 282 located on the side of the trocar 226 while the terminal 274d is connected to the ground. The terminal 276c of the internal connector 234 which is connected to the terminal 274c is connected to a communication control circuit 284 via a buffer 280 of the sensor confirming section 210. The arrangement of other components is the same as that shown in FIG. 25.

In the case of the components arrangement shown in FIG. 26, communication is exchanged between the trocar 226 and the insufflation unit 203 through the communication control circuits 282 and 284. It can be therefore confirmed at the insufflation unit 203 whether or not the pressure sensor 222 is connected and what kind of trocar 226 is used.

In FIG. 27, the pressure sensor 222 is connected to an A/D input terminal of a CPU 288, which has communication capacity, through a sensor amplifier 286. A communication terminal of the CPU 288 is connected to a CPU 290, which is arranged at the sensor confirming section 210, for example, of the insufflation unit 203, through internal connectors 232 and 234 which are the same in structure as those shown in FIG. 26. It may be arranged that the CPU 290 is connected to all of the control, display, input, drive and other means and that all functions of the insufflation unit 203 are controlled by the CPU 290.

In the case of the components arrangement shown in FIG. 27, the CPU 288 feeds signals through the communication line to inform the CPU 290 that the pressure sensor 222 is connected and what kind of the trocar 226 is used when the internal connectors 232 and 234 are connected to each other. More specifically, the pressure sensor 222 converts the pressure in the body cavity into an electric signal, which is amplified by the sensor amplifier 286 and inputted to the A/D input terminal of the CPU 288 where it is converted into a digital valve. The CPU 288 sends to the CPU 290 data relating to the connection of the pressure sensor 222, the kind of the trocar 226 used and the pressure in the body cavity, at a certain time interval or when any change is caused in pressure in the body cavity.

According to the components arrangement shown in FIG. 27, information obtained through the pressure sensor 222 is transmitted to the insufflation unit 203 through the communication system. This can prevent the insufflation unit from malfunctioning because of wrong data applied when a correct signal is inserted into data and when data is again transmitted.

The above-mentioned CPUs are incorporated, as one chip CPU, into the trocar 226 together with various kinds of sensor.

When temperature, humidity and other sensors are connected to the CPU 288, data relating to the temperature of the patient, humidity in his body cavity and others can be transmitted to the CPU 290 in the same manner as described above. When an LCD is used, the pressure in the body cavity can be displayed through the trocar 226.

In the case of a components arrangement shown in FIG. 28, information is applied from the pressure sensor 222 to the insufflation unit 203 through an optical communication system. Communication terminal output of the CPU 288 is connected to the input terminal of a driver 292, whose output is connected to an LED 294. The light receiving face of an optical fiber 296 is opposed to the light emitting face of the LED 294, while the light emitting face of the optical fiber 296 to the light receiving face of a phototransistor 298. The output of the phototransistor 298 is connected to the communication input terminal of the CPU 290 through a buffer amplifier 299.

When arranged as described above, the light emitting of LED 294 is controlled by communication output applied from the CPU 288 through the driver 292 and communication data is converted to a optical signal. The communication data transmitted, as the optical signal, through the optical fiber 296 enters into the phototransistor 298 where it is again returned to a electric signal. This electric signal is inputted to the communication input terminal of the CPU 290 through the buffer amplifier 299.

The circuit shown in FIG. 28 uses light as its communication means. The insufflation unit, therefore, can be kept sufficiently free from any noises emitted from external equipments such as the X-ray apparatus and the electric surgical knife in the operation room and it can be thus operated under a higher stability.

The communication lines shown in FIGS. 25 through 28 are of the one way type, enabling communication to be made only from the trocar 226 to the insufflation unit 203. It is therefore preferable to use the two-way communication type through which command is sent from the insufflation unit 203 to the trocar 226 to mark a relief system of the trocar 226, which will be described later, operative and through which alarm is sent to the trocar 226. Needless to say, half- and full-duplex communications may be employed and it is therefore optional whichever type of communications is employed.

As shown in FIG. 29, a relief valve 300 is arranged at the rear end portion of the trocar 226. A diaphragm 304 and a spring 306 are arranged in a housing 302 for the relief valve 300. the diaphragm 304 is urged by the spring 306 to close the inner pipe passage in the trocar 226.

The control of keeping the pressure in the body cavity at the value set is usually conducted in the insufflation unit 203. When the trocar 226 is to be used with a treatment tool 308 such as the electric surgical knife held therein, it sometimes happens that the pressure in the body cavity becomes higher than the value set because cooling $CO_2$ is fed into the body cavity, for example. The pressure in the body cavity pushes up the diaphragm 304 of the relief valve 300 against the spring 306 in this case to discharge excessive gas outside through an opening 302a of the housing 302. When the pressure in the body cavity returns lower than the value set, the urging force of the spring 306 exceeds the pressure in the body cavity to thereby cause the diaphragm 304 to again close the inner pipe passage of the trocar 226. The discharge of gas is thus stopped. When the pressure in the body cavity becomes abnormally high as described above, therefore, the relief valve 300 is automatically opened so that any state dangerous to the patient can be instantly avoided. In addition, a safer insufflation of gas can be achieved under high pressure and the insufflation of gas can also be achieved at a larger flow rate.

FIG. 30 shows a variation of the arrangement shown in FIG. 29. A solenoid valve 315 is used as the relief valve in this case. The solenoid valve 315 is electrically connected to the insufflation unit 203 through an electric line 310.

It is determined by the elastic modulus of the spring 306 whether or not the relief valve 300 is opened, and when the pressure at which the relief valve 300 is opened is 300 mmHg, for example, the relief valve 300 is not be opened unless the pressure in the body cavity exceeds 30 mmHg. When the solenoid valve 315 is used as the relief valve, however, it can be controlled by signals applied from the insufflation unit 203. This enables the opening pressure of the solenoid valve 315 to be set at any optional value.

When it is set 9 mmHg relative to the cavity pressure of 8 mmHg set or it is set 22 mmHg relative to the cavity pressure of 20 mmHg set, for example, the valve 315 can be opened at an optional value a littler larger than the value of the cavity pressure set.

When the trocar 226 is provided with the relief valve as described above, therefore, it is quite effective as follows: the gas insufflating pressure in the body cavity can be made high and gas can be thus instantly insufflated into the body cavity so as to achieve a shorter gas insufflating time and recover a sudden pressure fall in the body cavity, which is caused when sucking and other means are made operative, for a shorter time, and this can be more safely achieved without excessively adding pressure into the body cavity.

It will be described how the insufflation apparatus 201 having either of such components arrangements as described above is operated. As shown in FIG. 20, gas (or $CO_2$ gas) supplied from the gas bomb 202 at a pressure of several tens mmHg is reduced at first smaller than 1/10 by the decompression means 204. When the internal connectors 232 and 234 are connected to each other, the sensor confirming section 210 detects the connection of the pressure sensor 222 to the line and the first electromagnetic valve 254 is closed while the second one 252 is opened in the pressure/flow rate control section 206 through the changeover section 208.

The $CO_2$ gas decompressed through the decompression means 204 is further decompressed by the decompression means 258 in the pressure/flow rate control section 206 to such an extent (or 200 mmHg in this case) that a pressure safe to the patient and a flow rate not to disturb the surgical operation can be obtained. The $CO_2$ gas which has been reduced to 200 mmHg is insufflated into the body cavity through the pipe 218 and the trocar 226. The pressure rising in the body cavity is monitored by the pressure sensor 222 and information relating to this rising pressure is sent as electric signal to the pressure control section 212. Responsive to this electric signal, the pressure control section 212 opens the third electromagnetic valve 250 in the pressure/flow rate control section 206 until the pressure in the body cavity reaches a value of pressure (8 mmHg, for example) set. When the pressure in the body cavity reaches the value set, the third electromagnetic valve 250 in the pressure/flow rate control section 206 is closed via the pressure sensor 222 and the pressure control section 212, thereby stopping the gas insufflation into the body cavity.

when $CO_2$ gas is leaked from the body cavity by the surgical tools used in the surgical operation to thereby reduce the pressure in the body cavity, an electric signal asking gas to be insufflated into the body cavity is sent from the pressure control section 212, which monitors outputs of the pressure sensor 222 at all times, to the pressure/flow rate control section 206. The third electromagnetic valve 250 is thus again opened to insufflate gas into the body cavity. The pressure in the body cavity can be thus kept equal to the value of pressure set.

When the trocar 226 used has no pressure sensor 222, the same control as described above is made using the pressure sensor 220 in the pipe passage of the insufflated unit 203. Because the pressure of gas insufflated acts, as dynamic pressure, directly on the pressure sensor 220, however, it is needed that the measuring of the pressure in the body cavity by the pressure sensor 222 is conducted under static pressure while stopping the insufflation of gas and making the pipe 218 communicate with the body cavity. If the pressure in the body cavity does not reach the value of pressure set after this measuring of the pressure in the body cavity, the third electromagnetic valve 250 is opened through the pressure control section 212 to again insufflate gas into the body cavity. When the pressure in the body cavity is controlled by the pressure sensor 220 in this manner, the insufflation of gas and the measurement of the pressure in the body cavity are alternately repeated. The pressure in the body cavity is measured by the output side of the pressure sensor 220. When resistance in the pipe passage is changed because the pipe 218 is jammed or broken and when the pressure in the body cavity is thus detected lower than a true value of pressure by the pressure sensor 220, therefore, $CO_2$ gas insufflated into the body cavity becomes larger than the value of pressure set. This is dangerous to the patient. In order to avoid this danger, however, the first electromagnetic valve 254 is opened while the second electromagnetic valve 252 is closed at the pressure/flow rate control section 206 through the changeover section 208 every time the sensor confirming section 210 confirms that it is connected to the pressure sensor 220 (or, more exactly, that it is not connected to the pressure sensor 222). In short, the insufflation of gas can be conducted at a low pressure of 50 mmHg.

The pressure of gas insufflated has a close relation with the flow rate of gas insufflated. When the former is made low, the latter cannot be made large and the operator, therefore, feels it difficult to operate the apparatus because the time needed to insufflate gas into the body cavity becomes long. In other words, the safety of patients is contrary to the operating easiness of the apparatus.

when the pressure sensor 222 is used as described above, however, the static pressure in the body cavity can be measured without stopping the insufflation of gas into the body cavity. This enables the insufflation of gas to be made at a high pressure of 200 mmHg. A faster insufflation of gas is thus made possible. Even if the insufflation of gas is made at this high pressure, the patient can be kept safe because any change of the pressure in the body cavity is viewed at all times through the pressure control section 212.

AS described above, the insufflation apparatus 201 makes it possible to measure the static pressure in the body cavity without stopping the insufflation of gas into the body cavity. A more efficient insufflation of gas can be realized accordingly. In addition, any of the now-existing gas insufflating pipes can be effectively used because the pressure sensors 220 and 222 can be changed over by the changeover section 208 through the sensor confirming section 210.

various means can be imagined to detect any rise of pressure in the body cavity as soon as possible and to instantly deal with it to keep the patient safe. FIG. 31 shows one of them wherein four or five trocars 226 are stuck into the body cavity of a patient 339 while introducing a scope 325 into it through one of the trocars 226 and treating tools 330, 331 and 332 into it through the other trocars 226. A TV camera 326 is connected to the scope 325 and image signals picked up are viewed on a TV monitor 324 through a TV camera control unit 322. A fiber cable 327 which is connected to a light source unit 320 is connected to the scope 325 to send light into the body cavity.

The value of pressure set in the body cavity is usually about 10 mmHg and it does not exceed 20 mmHg. However, the pressure of gas insufflated through (the outlet of) the insufflation apparatus 1 is usually 50 mmHg and when the insufflation of gas is conducted at this pressure, it is quite dangerous to the patient.

In the case of the components arrangement shown in FIG. 31, however, at least two of the four trocars 226 are provided with spring-acted relief valves 335 and each of the relief valves 335 is made active at a different spring pressure. One of the relief valves 335 is made active at 30 mmHg and the other at 50 mmHg, for example. When provided in this manner, the relief valve 335 which is set active at 30 mmHg is opened at first to prevent excessive pressure from being added into the body cavity even if the pressure in the body cavity becomes excessive during the ordinary surgical operation. In a case where the pressure in the body cavity is made abnormally high by some causes, the relief valve 335 which is set active at 50 mmHg is opened to quickly discharge gas outside so as to reduce the pressure in the body cavity.

The relief valves 335 may be of the electromagnetic type. In this case, one of them serves to keep the pressure when the pressure of gas in the body cavity is near the value of pressure set, but the other is opened together with the one when high pressure is suddenly added into the body cavity. In other words, pressures and flow rates at which they are opened may be set and selected according to circumstances.

In the case of a components arrangement shown in FIG. 32, trocars 226 have first elements 348 used for transmission and reception (when the first elements 348 are used for reception, they are phototransistors, for example) and these trocars 226 also have solenoid valves. The are stuck in this case into a belly 349 of the patient. At least one of them is connected to the pipe 218 which is connected to the insufflation apparatus 201. An antenna 345 is located above a bed (not shown) on which the patient lies, and second plural transmitting and receiving elements 342 (when they are used for transmission, they are LEDs, for example) are attached to the antenna 345. They are connected to the insufflation apparatus 201 through a signal line 340.

In a case where the pressure in the body cavity becomes abnormally high when $CO_2$ gas is being insufflated from the insufflation apparatus 201 into the body cavity through the pipe 218, the insufflation apparatus 201 detects it and sends a signal to the second elements 342 through the signal line 340. This signal is transmitted to the first element 348 of each of the trocars 226 by the second elements 342. When the first elements 348 receive this signal, the solenoid valves in the trocars 226 are opened to discharge $CO_2$ gas outside so as to reduce the pressure in the body cavity. When the pressure in the body cavity is thus reduced lower than safe pressure or the value of pressure set, the insufflation apparatus 201 stops its applying of signal to the second elements 342. The solenoid valves in the trocars 226 are therefore closed.

It can be imagined in this case that first and second elements 348 and 342 are made transmittable and receivable (by forming each of them by a pair of a photo-transistor and an LED) and that pressure sensors as well as solenoid valves are arranged in the trocars 226 to transmit and receive data relating to pressures by wireless. It can be further imagined that a pressure sensor and a transmitting element are arranged only in one of the trocars 226 while a solenoid valve and a receiving element are arranged in each of the others and that transmitting and receiving elements are attached to the antenna 345. Various combinations can be imagined in this case and it depends upon circumstances which combination is employed.

when surgical operation is conducting with various kinds of treating tools scattered on the belly of the patient, it is quite advantageous from the viewpoint of sanitation and effiency that pressure sensor and solenoid valve drive signals are exchanged by wireless. Further, the transmitting and receiving elements are arranged above the bed. Even when some doctors surround the patient on the bed, therefore, transmission and reception of signals are not disturbed. Still further, when solar cells are used as electric ones housed in the trocars 226 and an astral lamp arranged above the bed serves as the antenna 345 provided with the transmitting and receiving elements, light energy emitted from the astral lamp can be received to produce electric power. The above-described signal transmission and reception are made using optical signals, but they may be modulated. Or they may be radio frequency or ultrasonic ones.

Figure 33:
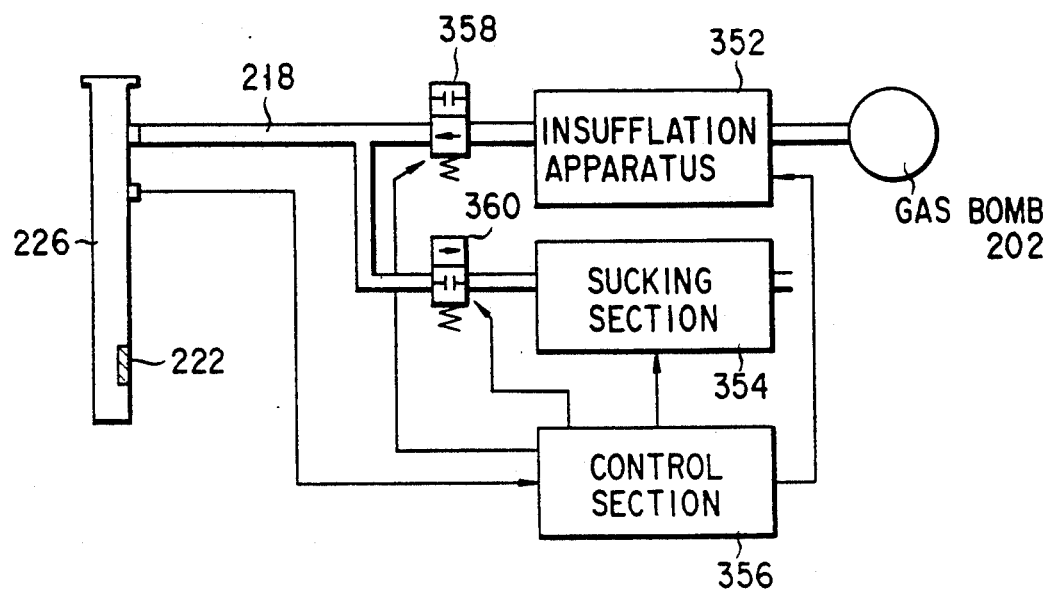
FIG. 33 schematically shows third danger preventing means employed by the insufflation apparatus.

In the case of a components arrangement shown in FIG. 33, $CO_2$ gas fed from a $CO_2$ gas bomb 202 is decompressed to an appropriate value of pressure by an insufflation apparatus 352 and the $CO_2$ gas which has been decompressed is insufflated into the body cavity through an electromagnetic valve 358 and the trocar 226. The pipe 218 branches midway and its forked path is connected to a sucking section 354 through an electromagnetic valve 360.

A signal is applied from the pressure sensor 222 of the trocar 226 to a control section 356, which is connected to the insufflation apparatus 352 and the sucking section 354 through signal lines to control them, if necessary. The electromagnetic valves 358 and 360 are connected to the control section 356 in such a way that they can be controlled independent of the other.

According to the components arrangement shown in FIG. 33, control section 356 closes the electromagnetic valve 358 to stop the insufflation of gas while it opens the electromagnetic valve 360 to drive the sucking section 354 so as to suck $CO_2$ gas in the body cavity, when the pressure in the body cavity becomes higher than a value of pressure set and the control section 356 detects signal applied from the pressure sensor 222. When $CO_2$ gas is sucked by the sucking section 354 and the pressure in the body cavity is thus rapidly made smaller than the value of pressure set or safe pressure, the control section 356 detects it to stop the sucking section 354 and close the electromagnetic valve 360, while it again opens the electromagnetic valve 358 to start the insufflation of gas.

This components arrangement shown in FIG. 33 also enables the patient to be protected from such a state that the pressure in his body cavity becomes so high as to bring him into danger. The measuring of the pressure in the body cavity may be made using the pressure sensor 220 which is arranged in the pipe 218 (see FIG. 20). It may also be arranged that the pipe 218 is not forked but that a sucking pipe is added and connected to the trocar 226.

Figure 34:
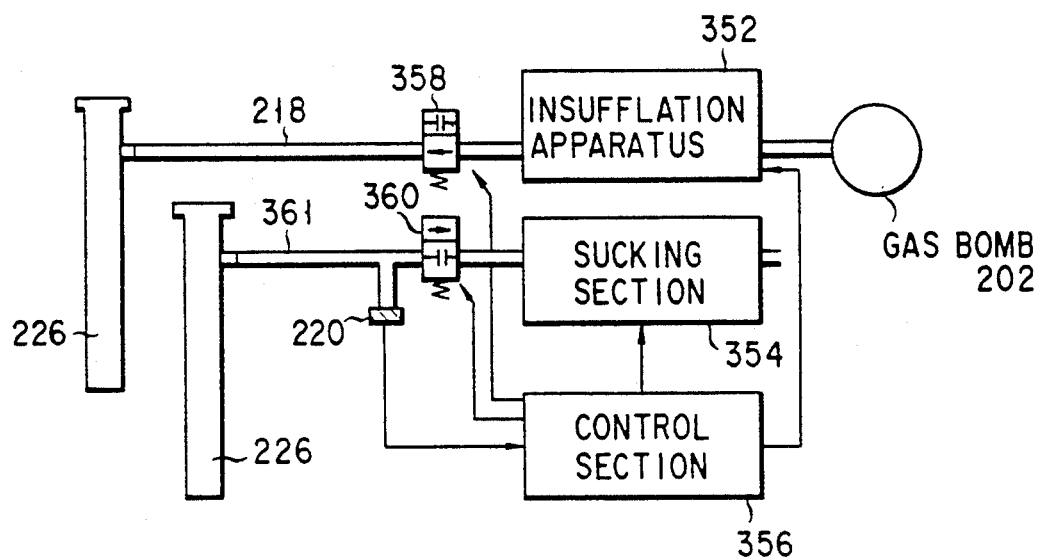
FIG. 34 schematically shows fourth danger preventing means employed by the insufflation apparatus.

In the case of a components arrangement shown in FIG. 34, the gas insufflating pipe 218 and a sucking pipe 361 are connected to their corresponding trocars 226 (which are inserted into a same area in the body cavity). The sucking pipe 361 is forked midway and the pressure sensor 220 is connected to its forked path. The output of the pressure sensor 220 is connected to the control section 356.

When the insufflation of gas is started in the same manner as seen in FIG. 33 and the pressure in the body cavity becomes abnormally high, the electromagnetic valve 358 is closed and the electromagnetic valve 360 is opened by the control section 356. The sucking section 354 is thus driven to decompress the pressure in the body cavity.

Different from the one shown in FIG. 33, the components arrangement shown in FIG. 34 enables insufflating and sucking operations to be made at the same time. Smoke caused by the laser and the surgical knife can be therefore discharged outside, while keeping the pressure in the body cavity certain. It is needed in this case that the sucking operation is stopped to measure the static pressure in the body cavity. However, this can be achieved when the electromagnetic valve 360 is closed. When the sucking operation is being conducted while keeping the electromagnetic valve 360 open, the dynamic sucking pressure is measured by the pressure sensor 220. This enables the sucking operation to be monitored. The patient can be therefore protected from such a state that the pressure in the body cavity becomes so high as to bring him into danger, and the reliability of the apparatus can also be made higher. Although two trocars 226 have been used in this case, both of the gas insufflating and sucking pipes may be connected to a trocar 226. Or both of the gas insufflating and sucking pipes may be combined to a multiplex pipe and this multiplex pipe may be connected to a trocar 226.

It should be understood that the present invention is not limited to the above-described embodiments but that various changes and modifications can be made without departing from the spirit and scope of the present invention.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An insufflation apparatus comprising:
a gas supply source filled with gas;
a gas insufflating pipe through which gas in the gas supply source is insufflated into a cavity of a human body;
a gas supply pipe through which gas supplied from the gas supply source is fed into the gas insufflating pipe;
a switch valve for opening and closing the gas supply pipe;
cavity pressure measuring means arranged in the gas supply pipe for measuring pressure in the body cavity;
pressure setting means for setting an intended pressure in the body cavity;
arithmetic means for calculating a difference of a value measured by the cavity pressure measuring means relative to a value of pressure set by the pressure setting means; and
control means for changing the duty cycle, during different periods in which the switch valve is opened and closed, on the basis of values calculated by the arithmetic means.

2. The insufflation apparatus according to claim 1, wherein said cavity pressure measuring means includes a tank filled with gas, means for controlling gas to come into and out of the tank, and means for measuring any change of the pressure in the tank, which is reduced when gas is discharged out of the tank, to calculate the pressure in the body cavity.

3. The insufflation apparatus according to claim 1, wherein said control means includes overshooting prevention means for preventing the pressure in the body cavity from exceeding the value of pressure set in such a way that the time during which the switch valve is opened is made shorter and shorter to decrease the flow rate of gas insufflated through the gas supply pipe.

4. The insufflation apparatus according to claim 1, wherein said control means includes first flow rate changing means for changing the flow rate of gas insufflated through the gas supply pipe by controlling the times during which the switch valve is opened and closed.

5. The insufflation apparatus according to claim 1, wherein said gas supply pipe includes a mass flow controller means for changing the flow rate of gas insufflated per a time unit through the gas supply pipe.

6. The insufflation apparatus according to claim 1, wherein said gas supply pipe includes a flow meter means for measuring the flow rate of gas flowing through the gas supply pipe and said control means includes first flow rate control means for controlling the times, during which the switch valve is opened and closed, on the basis of values measured by the flow meter means to control the flow rate of gas insufflated through the gas supply pipe.

7. The insufflation apparatus according to claim 6, wherein said control means includes first adjuster means for comparing the values measured by the flow meter means with those measured by the cavity pressure measuring means to control the duty cycle in which the switch valve is opened and closed and to adjust any error between the set amount of gas insufflated and an amount of gas insufflated said error being caused from the difference of passage resistances in the gas insufflating pipes used.

8. The insufflation apparatus according to claim 1, further comprising a pressure switch connected to the gas supply pipe; and means for making the pressure in the pipe connected to the pressure switch smaller than a pressure value at which the pressure switch is made operative.

9. An insufflation apparatus according to claim 1, further comprising plural flow rate adjusting pipes arranged in the gas supply pipe and having different flow rates per a time unit; pipe changeover means for optionally selecting at least one of the plural flow rate adjusting pipes to cause said at least one flow rate adjusting pipe to be opened; and changeover control means for controlling the pipe changeover means according to the flow rates of gas insufflated from the gas supply pipe to the gas insufflating pipe.

10. The insufflation apparatus according to claim 9, wherein said changeover control means includes overshooting prevention means for preventing the pressure in the body cavity from exceeding a value of pressure set in such a way that the pipe changeover means is controlled to change over the plural flow rate adjusting pipes from one another so as to reduce the flow rate of gas insufflated through the gas supply pipe.

11. The insufflation apparatus according to claim 9, wherein said changeover control means includes flow rate changing means for changing the flow rate of gas insufflated through the gas supply pipe in such a way that the pipe changeover means is controlled to change over the plural flow rate adjusting pipes from one another.

12. The insufflation apparatus according to claim 9, wherein at least one of the plural flow rate adjusting pipes includes a flow means for measuring the flow rate of gas insufflated through the flow rate adjusting pipe and said control means includes flow rate control means for controlling the times, during which the switch valve is opened and closed, on the basis of values measured by the flow meter means to control the flow rate of gas insufflated through the gas supply pipe.

13. The insufflation apparatus according to claim 12, wherein said control means includes adjuster means for comparing values measured by the flow meter with those measured by the cavity pressure measuring means to control the duty cycle in which the switch valve is opened and closed and to adjust any error between the set amount of gas insufflated and an amount of gas insufflated said error being caused from different passage resistances in the gas insufflating pipes used.

14. The insufflation apparatus according to claim 9, wherein said pipe changeover means includes an electromagnetic valve.

15. The insufflation apparatus according to claim 14, further comprising means for equally driving the electromagnetic and switch valves.

16. The insufflation apparatus according to claim 15, wherein said equally driving means includes a pulse counter.

17. The insufflation apparatus according to claim 1, further comprising plural flow rate adjusting pipes arranged in the gas supply pipe, each having a different flow rate per a time unit; and pipe changeover means for optionally selecting at least one of the plural flow rate adjusting pipes to cause said at least one flow rate adjusting pipe to be opened; and wherein said control means includes first flow rate reducing means for gradually making shorter and shorter the time during which the switch valve is opened to reduce the flow rate of gas insufflated through the gas supply pipe, second flow rate reducing means for controlling the pipe changeover means to change over the plural flow rate adjusting pipes from one another so as to reduce the flow rate of gas insufflated through the gas supply pipe, and overshooting prevention means for reducing the flow rate of gas insufflated through the gas supply pipe by the first and second flow rate reducing means to prevent the pressure in the body cavity from exceeding a value of pressure set.

18. The insufflation apparatus according to claim 1, further comprising plural flow rate adjusting pipes arranged in the gas supply pipe, each having a different flow rate per a time unit; and pipe changeover means for optionally selecting at least one of the plural flow rate adjusting pipes to cause said at least one flow rate adjusting pipe to be opened; and wherein said control means includes first flow rate changing means for controlling the times, during which the switch valve is opened and closed, to change the flow rate of gas insufflated through the gas supply pipe, second flow rate changing means for controlling the pipe changeover means to change over the plural flow rate adjusting pipes from one another so as to change the flow rate of gas insufflated through the gas supply pipe, and third flow rate changing means for changing the flow rate of gas insufflated through the gas supply pipe by the first and second flow rate changing means.

* * * * *